(12) United States Patent
Michalak et al.

(10) Patent No.: US 7,541,485 B2
(45) Date of Patent: Jun. 2, 2009

(54) METHODS FOR PREPARING GLUTAMIC ACID DERIVATIVES

(75) Inventors: Ronald S. Michalak, Congers, NY (US); Joseph Zeldis, New City, NY (US); Mel Jennings, Highland Falls, NY (US); David M. Blum, Upper Saddle River, NJ (US); Timothy Doyle, Morristown, NJ (US)

(73) Assignee: Wyeth, Madison, NJ (US)

( * ) Notice: Subject to any disclaimer, the term of this patent is extended or adjusted under 35 U.S.C. 154(b) by 111 days.

(21) Appl. No.: 11/484,217

(22) Filed: Jul. 11, 2006

(65) Prior Publication Data

US 2007/0088172 A1 Apr. 19, 2007

Related U.S. Application Data

(60) Provisional application No. 60/726,441, filed on Oct. 13, 2005.

(51) Int. Cl.
C07C 237/02 (2006.01)
(52) U.S. Cl. ...................... 558/267; 562/450
(58) Field of Classification Search ............... 558/267; 562/450
See application file for complete search history.

(56) References Cited

U.S. PATENT DOCUMENTS

| | | | |
|---|---|---|---|
| 2,440,649 | A | 4/1948 | Avakian et al. |
| 5,563,127 | A | 10/1996 | Amparo et al. |
| 5,597,825 | A | 1/1997 | Himmelsbach et al. |
| 5,618,825 | A | 4/1997 | Baldwin et al. |
| 5,648,368 | A | 7/1997 | Egbertson et al. |
| 5,698,538 | A | 12/1997 | Amparo et al. |
| 5,736,559 | A | 4/1998 | Himmelsbach et al. |
| 5,756,810 | A | 5/1998 | Baldwin et al. |
| 5,852,007 | A | 12/1998 | Chatterjee |
| 5,922,763 | A | 7/1999 | Himmelsbach et al. |
| 6,242,422 | B1 | 6/2001 | Karanewsky et al. |
| 6,306,840 | B1 | 10/2001 | Adams et al. |
| 6,376,538 | B1 | 4/2002 | Adams et al. |
| 6,528,655 | B1 * | 3/2003 | N'Zemba et al. ......... 548/338.1 |
| 6,605,608 | B1 | 8/2003 | Seko et al. |
| 6,624,152 | B2 | 9/2003 | Adams et al. |
| 6,630,512 | B2 | 10/2003 | Adams et al. |
| 6,723,711 | B2 | 4/2004 | Biediger et al. |
| 6,943,269 | B2 * | 9/2005 | Gabriel et al. ............ 564/153 |
| 2002/0019416 | A1 | 2/2002 | Fukami et al. |
| 2002/0091089 | A1 | 7/2002 | Karanewsky et al. |
| 2002/0169326 | A1 | 11/2002 | Fukami et al. |
| 2003/0013725 | A1 | 1/2003 | Seko et al. |
| 2003/0018016 | A1 | 1/2003 | Adams et al. |
| 2003/0083267 | A1 | 5/2003 | Adams et al. |
| 2003/0199692 | A1 | 10/2003 | Biediger et al. |
| 2003/0232806 | A1 | 12/2003 | Seko et al. |
| 2004/0009956 | A1 | 1/2004 | Pei et al. |
| 2004/0063959 | A1 | 4/2004 | Fukami et al. |
| 2004/0259804 | A1 | 12/2004 | Karanewsky |
| 2005/0049242 | A1 | 3/2005 | Robinson et al. |
| 2007/0043066 | A1 | 2/2007 | Sum et al. |
| 2008/0119670 | A1 * | 5/2008 | Doyle et al. ............ 564/211 |

FOREIGN PATENT DOCUMENTS

| | | |
|---|---|---|
| DE | 3332633 | 4/1985 |
| EP | 496378 | 7/1992 |
| EP | 751765 | 1/1997 |
| EP | 805796 | 11/1997 |
| EP | 854863 | 7/1998 |
| EP | 496378 A1 | 1/1999 |
| EP | 997147 | 5/2000 |
| EP | 1090912 | 4/2001 |
| EP | 1142867 | 10/2001 |
| EP | 1189881 | 3/2002 |
| EP | 1213288 | 6/2002 |
| GB | 1 108 819 | 4/1968 |
| GB | 2292149 | 2/1996 |
| JP | 06192199 | 7/1994 |
| JP | 11080191 | 3/1999 |
| JP | 11116541 | 4/1999 |
| JP | 2002145849 | 5/2002 |
| WO | WO 93/012074 A1 | 6/1993 |
| WO | WO-94/12181 | 6/1994 |
| WO | WO-95/24186 | 9/1995 |
| WO | WO-96/20689 | 7/1996 |
| WO | WO-96/22966 | 8/1996 |
| WO | WO-97/03951 | 2/1997 |
| WO | WO-97/21690 | 6/1997 |
| WO | WO-99/02146 | 1/1999 |
| WO | WO-99/48371 | 9/1999 |
| WO | WO-00/00470 | 1/2000 |
| WO | WO-00/23421 | 4/2000 |
| WO | WO-00/27808 | 5/2000 |
| WO | WO-00/68188 | 11/2000 |
| WO | WO-01/83445 | 11/2001 |
| WO | WO-01/90077 | 11/2001 |
| WO | WO-03/093498 | 11/2003 |
| WO | WO-2005/019167 | 3/2005 |
| WO | WO-2005/040355 | 5/2005 |
| WO | WO-2005/058808 | 6/2005 |
| WO | WO-2005/060456 | 7/2005 |
| WO | WO/20058/087215 A1 | 9/2005 |
| WO | WO 2007/118693 | 10/2007 |

OTHER PUBLICATIONS

Beyermann, et al., "Rapid Continuous Peptide Synthesis via FMOC Amino Acid Chloride Coupling and 4-(aminomethyl)piperidine Deblocking", Journal of Organic Chemistry, 55(2):721-728 (1990).
Habermehl, et al., "Synthesis of N-[(3-ethoxycarbonylmethyl)-cyclohexyl]-azetidin-2-yl-propionic Acid Hydrochloride", Zeitschrift Fuer Naturforschung, B: Chemical Sciences, 47(2):1779-1784 (1992).
Jobron, et al., "Solid-Phase Synthesis of New S-Glycoamino Acid Building Blocks", Organic Letters, 2(15):2265-2267 (2000).

(Continued)

Primary Examiner—Yong Chu
(74) Attorney, Agent, or Firm—Andrea Dorigo

(57) ABSTRACT

The present invention relates to novel methods for the preparation of glutamic acid derivatives and intermediates thereof, and such compounds prepared by the novel methods.

2 Claims, No Drawings

OTHER PUBLICATIONS

Moroder, et al., "Cytochrome C. Part I.: Synthesis of the Protected Hexadecapeptide (Sequence 1-16) of Baker's Yeast Iso-1-Cytochrome C", Biopolymers, 12(3):477-492 (1973).

Okada, et al., "Amino Acids and Peptides LVI: Synthesis of Pyrazinone Ring-Containing Opioid Mimetics and Examination of Their Opioid Receptor Binding Activity", Tetrahedron, 55(50):14391-14406 (1999).

Suresh Babu, et al., "(Fluoren-9-ylmethoxy)carbonyl (Fmoc) Amino Acid Azides: Synthesis, Isolation, Characterisation, Stability and Application to Synthesis of Peptides", J. Chem. Soc., Perkin Trust, 1:4328-4331 (2000).

Takahashi, et al., "Novel Matrix Metalloproteinase Inhibitors: Generation of Lead Compounds by the in Silico Fragment-Based Approah", Bioorganic & Medicinal Chemistry, 13(14):4527-4543 (2005).

Wen, et al., "Synthesis of 9-Fluorenylmethoxycarbonyl-Protected Amino Aldehydes", Tetrahedron: Asymmetry, 9(11):1855-1858 (1998).

International Search Report Issued in PCT/US2006/02892 on Nov. 14, 2006.

Leite et al, "Synthesis, anti-inflammatory and antimicrobial activities of new 1,2,4-oxadiazoles peptidomimetics", Il Farmaco, vol. 55, Issues 11-12, , Dec. 2000, pp. 719-724, Scheme 15g.

Kerwin, et al., "Hybrid Cholecystokinin (CCK) Antagonists: New Implications in the Design and Modification of CCK Antagonists", J. Med. Chem., 32:739-742 (1989).

Kuefner, et al., "Carboxypeptidase-Mediated Release of Methotrexate from Methotrexate α-Peptides", Biochemistry, 28:2288-2297 (1989).

International Search Report, Issued Apr. 27, 2007, in PCT/US2006/027066.

Abbaszade, I. et al., "Cloning anc Characterization of *ADAMTS11*, an Aggrecanase from the ADAMTS Family", *J Biol Chem*, 274(33):23443-23450 (1999).

Colige, A. et al., "cDNA Cloning and Expression of Bovine Procollagen I N-Proteinase: A New Member of the Superfamily of Zinc-Metalloproteinases with Binding Sites for Cells and Other Matrix Components", *Proc Natl Acad Sci USA*, 94:2374-2379 (1997).

Kuno, et al., "Molecular Cloning of a Gene Encoding a New Type of Metalloproteinase-disintegrin Family Protein with Thrombospondin Motifs as an Inflammation Associated Gene", *Journal of Biological Chemistry*, 272(1):556-562 (1997).

Tang, BL, "ADAMTS: a Novel Family of Extracellular Matrix Proteases", *Int J. Biochem Cell Biol*, 33:33-44 (2001).

Vazquez, F. et al., "METH-1, a Human Ortholog of ADAMTS-1, and METH-2 are Members of a New Family of Proteins with Angio-inhibitory Activity", *J Biol Chem*, 274(33):23349-23357 (1999).

Bergmann, E.D. and Goldschmidt, Z., Fluorinated a,a-Dialkylphenethylamines, J. Med. Chem. 11, 1242-1244 (1968).

Jirgensons, A. et al. A Practical Synthesis of tert-Alkylamines via the Ritter Reaction with Chloroacetonitrile, Synthesis 12, 1709-1712 (2000).

Edwards, S. and Marquardt, F. Molecular Rearrangements in the Course of Ritter Reactions, J. Org. Chem. 39 (13), 1963 (1974).

Augeri, et al., "Potent and Selective Non-Cysteine-Containing Inhibitors of Protein Farnesyltransferase", Journal of Medicinal Chemistry, 41(22):4288-4300 (1998).

Boger, et al., "Conformationally Restricted Analogues Designed for Selective Inhibition of GAR Tfase Versus Thymidylate Synthase or Dihydrofolate Reductase", Bioorg. Med. Chem., 8:1075-1086 (2000).

Database Caplus [Online], XP002413088, "Inhibitory Effect of Methotrexate on Matrix Metalloproteinase-1 (Collagenase) Production by Synovial Fibroblasts", Database Accession No. 1997:137341.

Martinelli, et al., "Methotrexate Analogues. 12. Synthesis and Biological Properties of Some Aza Homologues", Journal of Medicinal Chemistry, 22(7):869-874 (1979).

Piper, et al., "Syntheses of α- and γ-Substituted Amides, Peptides, and Esters of Methotrexate and Their Evaluation as Inhibitors of Folate Metabolism", Journal of Medicinal Chemistry, 25(2):182-187 (1982).

Springer, et al., "Optimization of Alkylating Agent Prodrugs Derived from Phenol and Aniline Mustards: A New Clinical Candidate Prodrug (ZD2767) for Antibody-Directed Enzyme Prodrug Therapy (ADEPT)", Journal of Medicinal Chemistry, 38(26):5051-5065 (1995).

PCT Invitation to Pay Additional Fees with Partial International Search Report from PCT Application No. PCT/US2006/027066.

Tejima, Masayuki et al., Synthesis of a New Series of Z-Amino Acid and Z-Dipeptide Chloromethyl Ketone Derivatives, Agr. Biol. Chem., 39(7), 1423-1426,1975.

* cited by examiner

METHODS FOR PREPARING GLUTAMIC ACID DERIVATIVES

CROSS REFERENCE TO RELATED APPLICATIONS

This application claims the benefit of priority under 35 U.S.C. §119(e) to U.S. Patent Application Ser. No. 60/726,441 filed on Oct. 13, 2005 and is hereby incorporated by reference in its entirety.

Throughout this application, various publications are referenced. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure, as it appears in the U.S. Patent and Trademark Office patent file or records, but otherwise reserves any and all copyright rights whatsoever.

FIELD OF THE INVENTION

The present invention relates to novel methods for the preparation of glutamic acid derivatives, which are useful as metalloproteinase inhibitors.

BACKGROUND OF THE INVENTION

Metalloproteinases, including matrix metalloproteinases and aggrecanases, are known to have a role in the breakdown of connective tissue. Matrix metalloproteinases ("MMPs") constitute a super family of proteolytic enzymes that are genetically related and capable of degrading almost all the constituents of extracellular matrix and basement membrane that restrict cell movement. Aggrecanases are members of the ADAMTS (A disintegrin and metalloproteinase with thrombospondin motifs) family of proteins. Aggrecanase-1 and aggrecanase-2 have been designated ADAMTS-4 and ADAMTS-5, respectively (Tang B L, *Int J Biochem Cell Biol* 2001, 33, 33-44).

The ADAMTS family is involved in cleaving aggrecan, a cartilage component also known as the large aggregating chondroitin sulphate proteoglycan (Abbaszade I et al., J Biol Chem 1999, 274, 23443-23450), procollagen processing (Colige A et al., Proc Natl Acad Sci USA 1997, 94, 2374-2379), angiogenesis (Vazquez F et al., J Biol Chem 1999, 274, 23349-23357), inflammation (Kuno K et al., J Biol Chem 1997, 272, 556-562) and tumor invasion (Masui T., et al., J Biol Chem 1997, 272, 556-562). MMPs have been shown to cleave aggrecan as well.

The loss of aggrecan has been implicated in the degradation of articular cartilage in arthritic diseases, for example osteoarthritis is a debilitating disease which affects at least 30 million Americans. Degradation of articular cartilage and the resulting chronic pain can severely reduce quality of life. An early and important characteristic of the osteoarthritic process is loss of aggrecan from the extracellular matrix, resulting in deficiencies in the biomechanical characteristics of the cartilage. Likewise, MMPs and aggrecanases are known to play a role in many disorders in which extracellular protein degradation or destruction occurs, such as cancer, asthma, chronic obstructive pulmonary disease ("COPD"), atherosclerosis, age-related macular degeneration, myocardial infarction, corneal ulceration and other ocular surface diseases, hepatitis, aortic aneurysms, tendonitis, central nervous system diseases, abnormal wound healing, angiogenesis, restenosis, cirrhosis, multiple sclerosis, glomerulonephritis, graft versus host disease, diabetes, inflammatory bowel disease, shock, invertebral disc degeneration, stroke, osteopenia, and periodontal diseases.

The glutamic acid derivatives and the preparation thereof are disclosed in a commonly assigned and co-pending U.S. patent application Ser. No. 60/697,590, filed on Jul. 11, 2005. There remains a need to find a more efficient method suitable for commercial manufacturing of the glutamic acid derivatives.

SUMMARY OF THE INVENTION

In one aspect, the invention provides novel methods as described in the appended claims for preparing a compound of formula (I) and intermediates thereof,

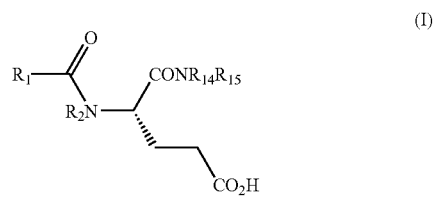

wherein:

$R_1$ is phenyl, heteroaryl, biphenyl, bicyclic aryl, tricyclic aryl, bicyclic heteroaryl, or tricyclic heteroaryl, each optionally substituted with one or more of $R_5$ or $R_6$, and when $R_1$ is substituted with more than one of $R_5$ or $R_6$, the substituents can be identical or different;

$R_2$ is hydrogen, $(C_1-C_6)$ alkyl, $(C_2-C_6)$ alkenyl, $(C_2-C_6)$ alkynyl, —$(CH_2)_n R_{11}$, —OH, or —O—$(C_1-C_6)$ alkyl;

$R_5$ is aryl, heteroaryl, —$(CH_2)_n$-aryl, —$(CH_2)_n$-heteroaryl, —O-aryl, —O-heteroaryl, —S-aryl, —S-heteroaryl, —NH-aryl, —NH-heteroaryl, —C(=O)—$(C_1-C_6)$ alkyl, —C(=O)-aryl, —C(=O)-heteroaryl, —$SO_2$—$(C_1-C_6)$ alkyl, —$SO_2$-aryl, —$SO_2$-heteroaryl, —$SO_2$NH-aryl, —$SO_2$NH-heteroaryl, —$NHSO_2$—$(C_1-C_6)$ alkyl, —$NHSO_2$-aryl, —$NHSO_2$-heteroaryl, —NHC(=O)-aryl, —NHC(=O)-heteroaryl, —C(=O)NH-aryl, —C(=O)NH-heteroaryl, $(C_1-C_6)$ alkyl, —O—$(C_1-C_6)$ alkyl, —S—$(C_1-C_6)$ alkyl, —NH—$(C_1-C_6)$ alkyl, —NHC(=O)—$(C_1-C_6)$ alkyl, —C(=O)NH—$(C_1-C_6)$ alkyl, —O—$(C_1-C_6)$ cycloalkyl, —S—$(C_1-C_6)$ cycloalkyl, —NH—$(C_1-C_6)$ cycloalkyl, —NHC(=O)—$(C_1-C_6)$ cycloalkyl, or —C(=O)NH—$(C_1-C_6)$ cycloalkyl; each alkyl, aryl, cycloalkyl, or heteroaryl optionally substituted with one or more of $R_6$, and when $R_5$ is substituted with more than one $R_6$, the substituents can be identical or different;

$R_6$ is hydrogen, halogen, —CN, —$OCF_3$, —$CF_3$, —$NO_2$, —OH, —SH, —$NR_7R_8$, —C(=O)$NR_7R_8$, —$NR_8$C(=O)$R_7$, —$NR_8CO_2R_7$, —$CO_2R_7$, —C(=O)$R_7$, —$SO_2$—$(C_1-C_6)$ alkyl, —$SO_2$-aryl, —$SO_2$-heteroaryl, —$SO_2R_7$, —$NR_7SO_2R_8$, —$SO_2NR_7R_8$; $(C_1-C_6)$ alkyl, —O—$(C_1-C_6)$ alkyl, —S—$(C_1-C_6)$ alkyl, —NH—$(C_1-C_6)$ alkyl, —NHC(=O)—$(C_1-C_6)$ alkyl, —C(=O)NH—$(C_1-C_6)$ alkyl, —O—$(C_1-C_6)$ cycloalkyl, —S—$(C_1-C_6)$ cycloalkyl, —NH—$(C_1-C_6)$ cycloalkyl, —NHC(=O)—$(C_1-C_6)$ cycloalkyl, —C(=O)NH—$(C_1-C_6)$ cycloalkyl, heterocycloalkyl, —$(C_1-C_6)$ alkyl-$OR_7$, $(C_2-C_6)$ alkynyl, $(C_2-C_6)$ alkenyl, —O—$(C_1-C_6)$ alkyl-cycloalkyl, —O-alkenyl, —O—($C_1$-$C_6$) alkyl substituted with aryl, aryl, heteroaryl, —($CH_2$)$_n$-aryl, —($CH_2$)$_n$-heteroaryl, —O-aryl, —O-heteroaryl, —S-aryl, or —S-heteroaryl; each alkyl, aryl, cycloalkyl, heterocycloalkyl, heteroaryl, alkenyl, or alkynyl optionally substituted with one or more of $R_{13}$;

$R_7$ and $R_8$ are each independently hydrogen, ($C_1$-$C_6$) alkyl, aryl, heteroaryl, ($C_2$-$C_6$) alkenyl, ($C_2$-$C_6$) alkynyl, cycloalkyl, —($CH_2$)$_n$-aryl, or —($CH_2$)$_n$-heteroaryl; or $R_7$ and $R_8$ together may form a five- to seven-membered cyclic group containing up to 3 heteroatoms selected from N, O, or S;

$R_{11}$ is aryl, heteroaryl, or cycloalkyl;

$R_{12}$ is halogen, —CN, —$OCF_3$, —$CF_3$, —$NO_2$, —OH, —SH, —$NR_7R_8$, —C(=O)$NR_7R_8$, —$NR_8$C(=O)$R_7$, —$NR_8CO_2R_7$, —$CO_2R_7$, —C(=O)$R_7$, —$SO_2$—($C_1$-$C_6$) alkyl, —$SO_2$-aryl, —$SO_2$-heteroaryl, —$SO_2R_7$, —$NR_7SO_2R_8$, —$SO_2NR_7R_8$, linear or branched or cyclic ($C_1$-$C_6$) alkyl, —O—($C_1$-$C_6$) alkyl, —S—($C_1$-$C_6$) alkyl, —NH—($C_1$-$C_6$) alkyl, heterocycloalkyl, —($C_1$-$C_6$) alkyl-$OR_7$, ($C_2$-$C_6$) alkynyl, ($C_2$-$C_6$) alkenyl, —O—($C_1$-$C_6$) alkylcycloalkyl, —O-alkenyl, —O—($C_1$-$C_6$) alkylaryl, aryl, heteroaryl, —($CH_2$)$_n$-aryl, —($CH_2$)$_n$-heteroaryl, —O-aryl, —O-heteroaryl, —S-aryl, —S-heteroaryl, each alkyl, aryl, cycloalkyl, heterocycloalkyl, heteroaryl, alkenyl, or alkynyl optionally substituted with one or more of $R_{13}$;

$R_{13}$ is halogen, —O—($C_1$-$C_6$) alkyl, —$CO_2$H, —OH, —$CF_3$, hydrogen, ($C_1$-$C_6$) alkyl, aryl, heteroaryl, ($C_2$-$C_6$) alkenyl, ($C_2$-$C_6$) alkynyl, cycloalkyl, cycloalkyl substituted with —OH, aryl substituted with —$NH_2$, aryl substituted with —O—($C_1$-$C_6$) alkyl, —($CH_2$)$_n$-aryl, or —($CH_2$)$_n$-heteroaryl;

$R_{14}$ and $R_{15}$ are each independently hydrogen, ($C_1$-$C_6$) alkyl, aryl, heteroaryl, ($C_2$-$C_6$) alkenyl, ($C_2$-$C_6$) alkynyl, cycloalkyl, heterocycloalkyl, —($CH_2$)$_n$-aryl, bicyclic aryl, tricyclic aryl, bicyclic heteroaryl, or tricyclic heteroaryl; each alkyl, aryl, cycloalkyl, heterocycloalkyl, or heteroaryl optionally substituted with one or more $R_{12}$; or $R_{14}$ and $R_{15}$ together may form a five- to seven-membered cyclic group containing up to 3 heteroatoms selected from N, O, or S;

$R_{16}$ is ($C_1$-$C_6$) alkyl; and n is 0, 1, 2, 3, or 4.

In another aspect, the invention provides a compound of formula (I) and intermediates thereof prepared by such novel methods.

FURTHER DESCRIPTION OF THE INVENTION

Definitions

All recitations of a group, such as alkyl, are understood for the purposes of this specification to encompass both substituted and unsubstituted forms.

The term "alkyl", as used herein, whether used alone or as part of another group, refers to a substituted or unsubstituted aliphatic hydrocarbon chain and includes, but is not limited to, straight and branched chains containing from 1 to 12 carbon atoms, or in some instances, from 1 to 6 carbon atoms, unless explicitly specified otherwise. For example, methyl, ethyl, propyl, isopropyl, butyl, i-butyl and t-butyl are encompassed by the term "alkyl." ($C_1$-$C_6$)-alkyl includes straight and branched chain aliphatic groups having from 1 to 6 carbons. Specifically included within the definition of "alkyl" are those aliphatic hydrocarbon chains that are optionally substituted. In one embodiment, an alkyl is optionally substituted with one or more of the following groups: —V-halogen, —V—($C_1$-$C_6$)-alkyl, —V—($C_2$-$C_6$)-alkenyl, —V—($C_2$-$C_6$)-alkynyl, —V—N(R')$_2$, methylenedioxo, ethylenedioxo, —V—$NHSO_2$R', —V—NR'C(=O)R', —V—$NHCO_2$R', —V—$NO_2$, —V—$SO_2$N(R')$_2$, —V—$SO_2$R', —V—OR', —V—C(=O)R', —V—$CO_2$R', —V—C(=O)N(R')$_2$, or —V—CN, wherein each R' is independently hydrogen, unsubstituted ($C_1$-$C_6$)-alkyl, or unsubstituted aryl; and wherein each V is independently a bond or ($C_1$-$C_6$)-alkyl.

The number of carbon atoms as used in the definitions herein refers to carbon backbone and carbon branching, but does not include carbon atoms of the substituents, such as alkoxy substitutions and the like.

The term "alkenyl", as used herein, whether used alone or as part of another group, refers to a substituted or unsubstituted hydrocarbon chain and includes, but is not limited to, straight and branched chains having 2 to 8 carbon atoms and containing at least one double bond. In one embodiment, the alkenyl moiety has 1 or 2 double bonds. Such alkenyl moieties may exist in the E or Z conformations and the compounds of this invention include both conformations. ($C_2$-$C_6$) alkenyl includes a 2 to 6 carbon straight or branched chain having at least one carbon-carbon double bond. Specifically included within the definition of "alkenyl" are those aliphatic hydrocarbon chains that are optionally substituted. In one embodiment, a heteroatom, such as O, S or N, attached to an alkenyl is not attached to a carbon atom that is bonded to a double bond. In one embodiment, an alkenyl is optionally substituted with one or more of the following groups: —V-halogen, —V—($C_1$-$C_6$)-alkyl, —V—($C_2$-$C_6$)-alkenyl, —V—($C_2$-$C_6$)-alkynyl, —V—N(R')$_2$, methylenedioxo, ethylenedioxo, —V—$NHSO_2$R', —V—NR'COR', —V—$NHCO_2$R', —V—$NO_2$, —V—$SO_2$N(R')$_2$, —V—$SO_2$R', —V—OR', —V—C(=O)R', —V—$CO_2$R', —V—C(=O)N(R')$_2$, or —V—CN, wherein each R' is independently hydrogen, unsubstituted ($C_1$-$C_6$)-alkyl, or unsubstituted aryl; and wherein each V is independently a bond or ($C_1$-$C_6$)-alkyl.

The term "alkynyl", as used herein, whether used alone or as part of another group, refers to a hydrocarbon moiety containing at least one carbon-carbon triple bond. ($C_2$-$C_6$) alkynyl includes a 2 to 6 carbon straight or branched chain having at least one carbon-carbon triple bond. In one embodiment, an alkynyl is optionally substituted with one or more of the following groups: —V-halogen, —V—($C_1$-$C_6$)-alkyl, —V—($C_2$-$C_6$)-alkenyl, —V—($C_2$-$C_6$)-alkynyl, —V—N(R')$_2$, methylenedioxo, ethylenedioxo, —V—$NHSO_2$R', —V—NR'C(=O)R', —V—$NHCO_2$R', —V—$NO_2$, —V—$SO_2$N(R')$_2$, —V—$SO_2$R', —V—OR', —V—C(=O)R', —V—$CO_2$R', —V—C(=O)N(R')$_2$, or —V—CN, wherein each R' is independently hydrogen, unsubstituted ($C_1$-$C_6$)-alkyl, or unsubstituted aryl; and wherein each V is independently a bond or ($C_1$-$C_6$)-alkyl.

The term "cycloalkyl" refers to a monocyclic, bicyclic, tricyclic, fused, bridged, or spiro monovalent saturated hydrocarbon ring system, wherein the carbon atoms are located inside or outside of the ring system, e.g., of 3-15 carbon atoms. Any suitable ring position of the cycloalkyl moiety may be covalently linked to the defined chemical structure. Examples of cycloalkyl moieties include, but are not limited to, cyclopropyl, cyclopropylmethyl, cyclobutyl, cyclopentyl, cyclohexyl, cyclohexylmethyl, cyclohexylethyl, cycloheptyl, norbornyl, adamantyl, spiro[4.5]decanyl, and homologs, isomers, and the like. $C_3$-$C_6$ cycloalkyl includes monocyclic, saturated rings of 3 to 6 carbons. In one embodiment, a cycloalkyl is optionally substituted with one or more of the following groups: —V-halogen, —V—($C_1$-$C_6$)-alkyl, —V—($C_2$-$C_6$)-alkenyl, —V—($C_2$-$C_6$)-alkynyl, —V—N(R')$_2$, methylenedioxo, ethylenedioxo, —V—NHSO$_2$R', —V—NR'C(=O)R', —V—NHCO$_2$R', —V—NO$_2$, —V—SO$_2$N(R')$_2$, —V—SO$_2$R', —V—OR', —V—C(=O)R', —V—CO$_2$R', —V—C(=O)N(R')$_2$, or —V—CN, wherein each R' is independently hydrogen, unsubstituted ($C_1$-$C_6$)-alkyl, or unsubstituted aryl; and wherein each V is independently a bond or ($C_1$-$C_6$)-alkyl.

"Heteroaryl" refers to a 5 to 6 membered aromatic heterocyclic ring which contains from 1 to 4 heteroatoms selected from the group consisting of oxygen, nitrogen, and sulfur atoms in the ring and may be fused with a carbocyclic or heterocyclic ring at any possible position (e.g. fused to one or more carbocyclic or heterocyclic rings, each having 5-8 ring atoms, the fused heterocyclic ring containing from 1 to 4 heteroatoms selected from the group consisting of oxygen, nitrogen, and sulfur atoms in the ring). Exemplary heteroaryl groups include, but are not limited to, furanyl, furazanyl, homopiperazinyl, imidazolinyl, isothiazolyl, isoxazolyl, oxadiazolyl, oxazolyl, pyrimidinyl, phenanthridinyl, pyranyl, pyrazinyl, pyrazolinyl, pyrazolyl, pyridazinyl, pyridooxazolyl, pyridoimidazolyl, pyridothiazolyl, pyridinyl, pyrimidinyl, pyrrolinyl, thiadiazinyl, thiadiazolyl, thienyl, thienothiazolyl, thienooxazolyl, thienoimidazolyl, thiophenyl, triazinyl, and triazolyl. In one embodiment, a heteroaryl is optionally substituted with one or more of the following groups: —V-halogen, —V—($C_1$-$C_6$)-alkyl, —V—($C_2$-$C_6$)-alkenyl, —V—($C_2$-$C_6$)-alkynyl, —V—N(R')$_2$, methylenedioxo, ethylenedioxo, —V—NHSO$_2$R', —V—NR'C(=O)R', —V—NHCO$_2$R', —V—NO$_2$, —V—SO$_2$N(R')$_2$, —V—SO$_2$R', —V—OR', —V—C(=O)R', —V—CO$_2$R', —V—C(=O)N(R')$_2$, or —V—CN, wherein each R' is independently hydrogen, unsubstituted ($C_1$-$C_6$)-alkyl, or unsubstituted aryl; and wherein each V is independently a bond or ($C_1$-$C_6$)-alkyl.

"Heterocycloalkyl" refers to a 5 to 7-membered saturated ring containing carbon atoms and from 1 to 4 heteroatoms selected from N, O, and S. Exemplary heterocycloalkyl groups include, but are not limited to, azepanyl, azetidinyl, aziridinyl, imidazolidinyl, morpholinyl, oxazolidinyl, oxazolidinyl, piperazinyl, piperidinyl, pyrazolidinyl, pyrrolidinyl, quinuclidinyl, tetrahydrofuranyl, and thiomorpholinyl. In one embodiment, a heterocycloalkyl is optionally substituted with one or more of the following: —V-halogen, —V—($C_1$-$C_6$)-alkyl, —V—($C_2$-$C_6$)-alkenyl, —V—($C_2$-$C_6$)-alkynyl, —V—N(R')$_2$, methylenedioxo, ethylenedioxo, —V—NHSO$_2$R', —V—NR'C(=O)R', —V—NHCO$_2$R', —V—NO$_2$, —V—SO$_2$N(R')$_2$, —V—SO$_2$R', —V—OR', —V—C(=O)R', —V—CO$_2$R', —V—C(=O)N(R')$_2$, or —V—CN, wherein each R' is independently hydrogen, unsubstituted ($C_1$-$C_6$)-alkyl, or unsubstituted aryl; and wherein each V is independently a bond or ($C_1$-$C_6$)-alkyl.

The term "aryl" as used herein as a group or part of a group refers to an aromatic carbocyclic ring system, e.g., of from 6 to 14 carbon atoms such as phenyl, which may be optionally substituted. An aryl group may be fused with a carbocyclic or heterocyclic ring at any possible position (e.g. fused to one or more carbocyclic or heterocyclic rings, each having 5-8 ring atoms, the fused heterocyclic ring containing from 1 to 4 heteroatoms selected from the group consisting of oxygen, nitrogen, and sulfur atoms in the ring). "Phenyl", as used herein, whether used alone or as part of another group, refers to a substituted or unsubstituted phenyl group. In one embodiment, an aryl group such as phenyl is optionally substituted with one or more of the following: —V-halogen, —V—($C_1$-$C_6$)-alkyl, —V—($C_2$-$C_6$)-alkenyl, —V—($C_2$-$C_6$)-alkynyl, —V—N(R')$_2$, methylenedioxo, ethylenedioxo, —V—NHSO$_2$R', —V—NR'C(=O)R', —V—NHCO$_2$R', —V—NO$_2$, —V—SO$_2$N(R')$_2$, —V—SO$_2$R', —V—OR', —V—C(=O)R', —V—CO$_2$R', —V—C(=O)N(R')$_2$, or —V—CN, wherein each R' is independently hydrogen, unsubstituted ($C_1$-$C_6$)-alkyl, or unsubstituted aryl; and wherein each V is independently a bond or ($C_1$-$C_6$)-alkyl.

The term "biphenyl" as used herein refers to two phenyl groups connected at one carbon site on each ring. In one embodiment, one or both phenyl groups is independently optionally substituted with one or more of the following groups: —V-halogen, —V—($C_1$-$C_6$)-alkyl, —V—($C_2$-$C_6$)-alkenyl, —V—($C_2$-$C_6$)-alkynyl, —V—N(R')$_2$, methylenedioxo, ethylenedioxo, —V—NHSO$_2$R', —V—NR'C(=O)R', —V—NHCO$_2$R', —V—NO$_2$, —V—SO$_2$N(R')$_2$, —V—SO$_2$R', —V—OR', —V—C(=O)R', —V—CO$_2$R', —V—C(=O)N(R')$_2$, or —V—CN, wherein each R' is independently hydrogen, unsubstituted ($C_1$-$C_6$)-alkyl, or unsubstituted aryl; and wherein each V is independently a bond or ($C_1$-$C_6$)-alkyl.

The term "biaryl" as used herein refers to two aryl groups connected at one carbon site on each ring. In one embodiment, one or both aryl groups is independently optionally substituted with one or more of the following groups: —V-halogen, —V—($C_1$-$C_6$)-alkyl, —V—($C_2$-$C_6$)-alkenyl, —V—($C_2$-$C_6$)-alkynyl, —V—N(R')$_2$, methylenedioxo, ethylenedioxo, —V—NHSO$_2$R', —V—NR'C(=O)R', —V—NHCO$_2$R', —V—NO$_2$, —V—SO$_2$N(R')$_2$, —V—SO$_2$R', —V—OR', —V—C(=O)R', —V—CO$_2$R', —V—C(=O)N(R')$_2$, or —V—CN, wherein each R' is independently hydrogen, unsubstituted ($C_1$-$C_6$)-alkyl, or unsubstituted aryl; and wherein each V is independently a bond or ($C_1$-$C_6$)-alkyl.

The term "bicyclic aryl" as used herein refers to two fused carbocyclic groups, wherein one or both of the carbocyclic groups is aromatic. For example, a bicyclic aryl can contain from 8 to 12 ring atoms. In one embodiment, one or both carbocyclic groups of the bicyclic aryl is independently optionally substituted with one or more of the following groups: —V-halogen, —V—($C_1$-$C_6$)-alkyl, —V—($C_2$-$C_6$)-alkenyl, —V—($C_2$-$C_6$)-alkynyl, —V—N(R')$_2$, methylenedioxo, ethylenedioxo, —V—NHSO$_2$R', —V—NR'C(=O)R', —V—NHCO$_2$R', —V—NO$_2$, —V—SO$_2$N(R')$_2$, —V—SO$_2$R', —V—OR', —V—C(=O)R', —V—CO$_2$R', —V—C(=O)N(R')$_2$, or —V—CN, wherein each R' is independently hydrogen, unsubstituted ($C_1$-$C_6$)-alkyl, or unsubstituted aryl; and wherein each V is independently a bond or ($C_1$-$C_6$)-alkyl.

The term "tricyclic aryl" as used herein refers to three fused carbocyclic groups, wherein two or three of the carbocyclic groups is aromatic. For example, a tricyclic aryl can contain from 13 to 18 ring atoms. In one embodiment, one or more of the carbocyclic groups of the tricyclic aryl are independently optionally substituted with one or more of the following groups: —V-halogen, —V—($C_1$-$C_6$)-alkyl, —V—($C_2$-$C_6$)-alkenyl, —V—($C_2$-$C_6$)-alkynyl, —V—N(R')$_2$, methylenedioxo, ethylenedioxo, —V—NHSO$_2$R', —V—NR'C(=O)R', —V—NHCO$_2$R', —V—NO$_2$, —V—SO$_2$N(R')$_2$, —V—SO$_2$R', —V—OR', —V—C(=O)R', —V—CO$_2$R', —V—C(=O)N(R')$_2$, or —V—CN, wherein each R' is independently hydrogen, unsubstituted ($C_1$-$C_6$)-alkyl, or unsubstituted aryl; and wherein each V is independently a bond or ($C_1$-$C_6$)-alkyl.

The term "bicyclic heteroaryl" as used herein refers to two fused cyclic groups, wherein one or both of the cyclic groups is aromatic and contains one to four heteroatoms selected from O, S, and N. For example, a bicyclic heteroaryl can contain from 8 to 12 ring atoms, and from 1 to 3 heteroatoms selected from O, N, and S in each ring. In one embodiment, one or both cyclic groups is independently optionally substituted with one or more of the following groups: —V-halogen, —V—$(C_1-C_6)$-alkyl, —V—$(C_2-C_6)$-alkenyl, —V—$(C_2-C_6)$-alkynyl, —V—$N(R')_2$, methylenedioxo, ethylenedioxo, —V—$NHSO_2R'$, —V—$NR'C(=O)R'$, —V—$NHCO_2R'$, —V—$NO_2$, —V—$SO_2N(R')_2$, —V—$SO_2R'$, —V—OR', —V—$C(=O)R'$, —V—$CO_2R'$, —V—$C(=O)N(R')_2$, or —V—CN, wherein each R' is independently hydrogen, unsubstituted $(C_1-C_6)$-alkyl, or unsubstituted aryl; and wherein each V is independently a bond or $(C_1-C_6)$-alkyl.

The term "tricyclic heteroaryl" as used herein refers to three fused cyclic groups, wherein two or three of the cyclic groups is aromatic and at least one aromatic group contains 1 to 4 heteroatoms selected from O, S, and N. For example, a tricyclic aryl can contain from 13 to 18 ring atoms, and from 1 to 3 heteroatoms selected from O, N, and S in each ring. In one embodiment, the cyclic groups are independently substituted with one or more of the following groups: —V-halogen, —V—$(C_1-C_6)$-alkyl, —V—$(C_2-C_6)$-alkenyl, —V—$(C_2-C_6)$-alkynyl, —V—$N(R')_2$, methylenedioxo, ethylenedioxo, —V—$NHSO_2R'$, —V—$NR'C(=O)R'$, —V—$NHCO_2R'$, —V—$NO_2$, —V—$SO_2N(R')_2$, —V—$SO_2R'$, —V—OR', —V—$C(=O)R'$, —V—$CO_2R'$, —V—$C(=O)N(R')_2$, or —V—CN, wherein each R' is independently hydrogen, unsubstituted $(C_1-C_6)$-alkyl, or unsubstituted aryl; and wherein each V is independently a bond or $(C_1-C_6)$-alkyl.

An optionally substituted moiety may be substituted with one or more substituents, examples of which are as illustrated herein. In one embodiment, an "optionally substituted" moiety is substituted with one or more of the following: —V-halogen, —V—$(C_1-C_6)$-alkyl, —V—$(C_2-C_6)$-alkenyl, —V—$(C_2-C_6)$-alkynyl, —V—$N(R')_2$, methylenedioxo, ethylenedioxo, —V—$NHSO_2R'$, —V—$NR'C(=O)R'$, —V—$NHCO_2R'$, —V—$NO_2$, —V—$SO_2N(R')_2$, —V—$SO_2R'$, —V—OR', —V—$C(=O)R'$, —V—$CO_2R'$, —V—$C(=O)N(R')_2$, or —V—CN, wherein each R' is independently hydrogen, unsubstituted $(C_1-C_6)$-alkyl, or unsubstituted aryl; and wherein each V is independently a bond or $(C_1-C_6)$-alkyl.

When such moieties are substituted, for example, they may typically be mono-, di-, tri- or persubstituted. Examples for a halogen substituent include 1-bromo vinyl, 1-fluoro vinyl, 1,2-difluoro vinyl, 2,2-difluorovinyl, 1,2,2-trifluorovinyl, 1,2-dibromo ethane, 1,2 difluoro ethane, 1-fluoro-2-bromo ethane, $CF_2F_3$, $CF_2CF_2CF_3$, and the like.

The term halogen includes bromine, chlorine, fluorine, and iodine.

For the sake of simplicity, connection points ("–") are not depicted. When an atom or compound is described to define a variable, it is understood that it is intended to replace the variable in a manner to satisfy the valency of the atom or compound. For example, if "X*" was $C(R^*)=C(R^*)$, both carbon atoms form a part of the ring in order to satisfy their respective valences. Likewise, when divalent substituents are presented, it is understood that they are not limited to the order listed, for example, as used in this specification "$OCH_2$" encompasses $CH_2O$ and $OCH_2$.

The term "amine protecting group" as used herein refers to a moiety that temporarily blocks an amine reactive site in a compound. Generally, this is done so that a chemical reaction can be carried out at another reactive site in a multifunctional compound or to otherwise stabilize the amine. In one embodiment, an amine protecting group is selectively removable by a chemical reaction. An exemplary amine protecting group is a 9-fluorenylmethoxycarbonyl protecting group. Another exemplary amine protecting group is a carbamate protecting group. Carbamate protecting groups include, without limitation, t-butyl carbamate, methyl carbamate, ethyl carbamate, 2,2,2-trichloroethyl carbamate, 2-(trimethylsilyl)ethyl carbamate, 1,1-dimethyl-2,2,2-trichloroethyl carbamate, benzyl carbamate, p-methoxybenzyl carbamate, p-nitrobenzylcarbamate, p-bromobenzyl carbamate, p-chlorobenzyl carbamate, and 2,4-dichlorobenzyl carbamate. See, Greene and Wuts, *Protecting Groups in Organic Synthesis*, Third Edition, John Wiley & Sons (1999).

The term "carboxylic acid protecting group" as used herein refers to a moiety that temporarily blocks a carboxylic acid reactive site in a compound. Generally, this is done so that a chemical reaction can be carried out at another reactive site in a multifunctional compound or to otherwise stabilize the carboxylic acid. In one embodiment, a carboxylic acid protecting group is selectively removable by a chemical reaction. An exemplary carboxylic acid protecting group is an alkyl ester protecting group, such as a tert-butyl ester. See, Greene and Wuts, *Protecting Groups in Organic Synthesis*, Third Edition, John Wiley & Sons (1999).

The term "metalloproteinase-related disorder" used herein refers to a condition for which it would be beneficial to modulate activity of the metalloproteinase. Exemplary metalloproteinase-related disorders include, without limitation, arthritic disorders, osteoarthritis, cancer, rheumatoid arthritis, asthma, chronic obstructive pulmonary disease, atherosclerosis, age-related macular degeneration, myocardial infarction, corneal ulceration and other ocular surface diseases, hepatitis, aortic aneurysms, tendonitis, central nervous system diseases, abnormal wound healing, angiogenesis, restenosis, cirrhosis, multiple sclerosis, glomerulonephritis, graft versus host disease, diabetes, inflammatory bowel disease, shock, invertebral disc degeneration, stroke, osteopenia, and periodontal diseases.

The term "metalloproteinase modulator" refers to a compound that is capable of modulating the expression of a metalloproteinase. For example, a metalloproteinase modulator may enhance metalloproteinase expression. A metalloproteinase modulator may also be an inhibitor of a metalloproteinase.

The term "isolated and purified" as used herein refers to an isolate that is separate from other components of a reaction mixture or a natural source. In certain embodiments, the isolate contains at least about 50%, at least about 55%, at least about 60%, at least about 65%, at least about 70%, at least about 75%, at least about 80%, at least about 85%, at least about 90%, at least about 95%, or at least about 98% of the compound or pharmaceutically acceptable salt of the compound by weight of the isolate.

As used herein, a compound of the invention includes a pharmaceutically acceptable salt thereof. The term "pharmaceutically acceptable salt" as used herein refers to a salt of an acid and a basic nitrogen atom of a compound of the present invention. Exemplary salts include, but are not limited to, sulfate, citrate, acetate, oxalate, chloride, hydrochloride, bromide, hydrobromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, succinate, fumarate, maleate, malonate, mandelate, malate, phthalate, and pamoate. The term "pharmaceutically acceptable salt" as used herein also refers to a salt of a compound of the present invention having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like. The term "pharmaceutically acceptable salt" also includes a hydrate of a compound of the present invention.

The term "substantially free of its corresponding opposite enantiomer" as used herein means that the compound contains no more than about 10% by weight of its corresponding opposite enantiomer. In other embodiments, the compound that is substantially free of its corresponding opposite enantiomer contains no more than about 5%, no more than about 1%, no more than about 0.5%, or no more than about 0.1% by weight of its corresponding opposite enantiomer. An enantiomer that is substantially free of its corresponding opposite enantiomer includes a compound that has been isolated and purified or has been prepared substantially free of its corresponding opposite enantiomer.

The term "tautomer" as used herein refers to compounds produced by the phenomenon wherein a proton of one atom of a molecule shifts to another atom. See, Jerry March, *Advanced Organic Chemistry: Reactions, Mechanisms and Structures*, Fourth Edition, John Wiley & Sons, pages 69-74 (1992).

The following abbreviations as used herein mean:

Ac is acetate;

ACN is acetonitrile;

Boc is t-butyl carbamate;

Bu is butyl;

DEA is diethylamine;

DIEA is diisopropylethylamine;

DME is dimethoxyethane;

DMF is dimethylformamide;

DMSO is dimethylsulfoxide;

Et is ethyl;

Fmoc is 9-fluorenylmethoxycarbonyl;

HPLC is high pressure liquid chromatography;

HRMS is high resolution mass spectrometry;

IPA is isopropyl alcohol;

LCMS is liquid chromatograph-mass spectrometry;

Me is methyl;

MS is mass spectrometry;

m/z is mass-to-charge ratio;

NMM is N-methylmorpholine;

NMR is nuclear magnetic resonance;

r.t. is retention time;

TBME is t-butyl methyl ether;

TFA is trifluoroacetic acid; and

THF is tetrahydrofuran.

Compounds and Pharmaceutically Acceptable Salts of Compounds of the Invention

The compounds or pharmaceutically acceptable salts of compounds of the present invention contain an asymmetric carbon atom and some of the compounds or pharmaceutically acceptable salts of compounds of the invention can contain more than one asymmetric centers or no asymmetric centers, and can thus give rise to optical isomers, diastereomers and racemic mixtures. While depicted with or without respect to a particular asymmetric center in the compounds or pharmaceutically acceptable salts of compounds of the present invention, the present invention includes such optical isomers and diastereomers, as well as racemic and resolved, enantiomerically pure R and S stereoisomers, and also other mixtures of the R and S stereoisomers and pharmaceutically acceptable salts thereof. Where a stereoisomer is provided, it can in some embodiments be provided substantially free of its corresponding opposite enantiomer.

In addition, the compounds and pharmaceutically acceptable salts of compounds of the present invention can exist as tautomers. Such tautomers can be transient or isolatable as a stable product. These tautomers are within the scope of the present invention.

Prodrugs of the compounds or pharmaceutically acceptable salts of compounds are also within the scope of the present invention.

FURTHER ILLUSTRATION OF THE PRESENT INVENTION

For compounds of formulas (I) through (VII) and all reagents used in the preparation thereof, and throughout the specification, the symbols are defined as follows unless otherwise noted:

$R_1$ is phenyl, heteroaryl, biphenyl, bicyclic aryl, tricyclic aryl, bicyclic heteroaryl, or tricyclic heteroaryl, each optionally substituted with one or more of $R_5$ or $R_6$, and when $R_1$ is substituted with more than one of $R_5$ or $R_6$, the substituents can be identical or different;

$R_2$ is hydrogen, ($C_1$-$C_6$) alkyl, ($C_2$-$C_6$) alkenyl, ($C_2$-$C_6$) alkynyl, —($CH_2$)$_n R_{11}$, —OH, or —O—($C_1$-$C_6$) alkyl;

$R_5$ is aryl, heteroaryl, —($CH_2$)$_n$-aryl, —($CH_2$)$_n$-heteroaryl, —O-aryl, —O-heteroaryl, —S-aryl, —S-heteroaryl, —NH-aryl, —NH-heteroaryl, —C(=O)—($C_1$-$C_6$) alkyl, —C(=O)-aryl, —C(=O)-heteroaryl, —$SO_2$—($C_1$-$C_6$) alkyl, —$SO_2$-aryl, —$SO_2$-heteroaryl, —$SO_2$NH-aryl, —$SO_2$NH-heteroaryl, —$NHSO_2$—($C_1$-$C_6$) alkyl, —$NHSO_2$-aryl, —$NHSO_2$-heteroaryl, —NHC(=O)-aryl, —NHC(=O)-heteroaryl, —C(=O)NH-aryl, —C(=O)NH-heteroaryl, ($C_1$-$C_6$) alkyl, —O—($C_1$-$C_6$) alkyl, —S—($C_1$-$C_6$) alkyl, —NH—($C_1$-$C_6$) alkyl, —NHC(=O)—($C_1$-$C_6$) alkyl, —C(=O)NH—($C_1$-$C_6$) alkyl, —O—($C_1$-$C_6$) cycloalkyl, S—($C_1$-$C_6$) cycloalkyl, —NH—($C_1$-$C_6$) cycloalkyl, —NHC(=O)—($C_1$-$C_6$) cycloalkyl, or —C(=O)NH—($C_1$-$C_6$) cycloalkyl; each alkyl, aryl, cycloalkyl, or heteroaryl optionally substituted with one or more of $R_6$, and when $R_5$ is substituted with more than one $R_6$, the substituents can be identical or different;

$R_6$ is hydrogen, halogen, —CN, —$OCF_3$, —$CF_3$, —$NO_2$, —OH, —SH, —$NR_7R_8$, —C(=O)$NR_7R_8$, —$NR_8$C(=O)$R_7$, —$NR_8CO_2R_7$, —$CO_2R_7$, —C(=O)$R_7$, —$SO_2$—($C_1$-$C_6$) alkyl, —$SO_2$-aryl, —$SO_2$-heteroaryl, —$SO_2R_7$, —$NR_7SO_2R_8$, —$SO_2NR_7R_8$; ($C_1$-$C_6$) alkyl, —O—$(C_1\text{-}C_6)$ alkyl, —S—$(C_1\text{-}C_6)$ alkyl, —NH—$(C_1\text{-}C_6)$ alkyl, —NHC(=O)—$(C_1\text{-}C_6)$ alkyl, —C(=O)NH—$(C_1\text{-}C_6)$ alkyl, —O—$(C_1\text{-}C_6)$ cycloalkyl, —S—$(C_1\text{-}C_6)$ cycloalkyl, —NH—$(C_1\text{-}C_6)$ cycloalkyl, —NHC(=O)—$(C_1\text{-}C_6)$ cycloalkyl, —C(=O)NH—$(C_1\text{-}C_6)$ cycloalkyl, heterocycloalkyl, —$(C_1\text{-}C_6)$ alkyl-$OR_7$, $(C_2\text{-}C_6)$ alkynyl, $(C_2\text{-}C_6)$ alkenyl, —O—$(C_1\text{-}C_6)$ alkyl-cycloalkyl, —O-alkenyl, —O—$(C_1\text{-}C_6)$ alkyl substituted with aryl, aryl, heteroaryl, —$(CH_2)_n$-aryl, —$(CH_2)_n$-heteroaryl, —O-aryl, —O-heteroaryl, —S-aryl, or —S-heteroaryl; each alkyl, aryl, cycloalkyl, heterocycloalkyl, heteroaryl, alkenyl, or alkynyl optionally substituted with one or more of $R_{13}$;

$R_7$ and $R_8$ are each independently hydrogen, $(C_1\text{-}C_6)$ alkyl, aryl, heteroaryl, $(C_2\text{-}C_6)$ alkenyl, $(C_2\text{-}C_6)$ alkynyl, cycloalkyl, —$(CH_2)_n$-aryl, or —$(CH_2)_n$-heteroaryl; or $R_7$ and $R_8$ together may form a five- to seven-membered cyclic group containing up to 3 heteroatoms selected from N, O, or S;

$R_{11}$ is aryl, heteroaryl, or cycloalkyl;

$R_{12}$ is halogen, —CN, —$OCF_3$, —$CF_3$, —$NO_2$, —OH, —SH, —$NR_7R_8$, —C(=O)$NR_7R_8$, —$NR_8$C(=O)$R_7$, —$NR_8CO_2R_7$, —$CO_2R_7$, —C(=O)$R_7$, —$SO_2$—$(C_1\text{-}C_6)$ alkyl, —$SO_2$-aryl, —$SO_2$-heteroaryl, —$SO_2R_7$, —$NR_7SO_2R_8$, —$SO_2NR_7R_8$, linear or branched or cyclic $(C_1\text{-}C_6)$ alkyl, —O—$(C_1\text{-}C_6)$ alkyl, —S—$(C_1\text{-}C_6)$ alkyl, —NH—$(C_1\text{-}C_6)$ alkyl, heterocycloalkyl, —$(C_1\text{-}C_6)$ alkyl-$OR_7$, $(C_2\text{-}C_6)$ alkynyl, $(C_2\text{-}C_6)$ alkenyl, —O—$(C_1\text{-}C_6)$ alkylcycloalkyl, —O-alkenyl, —O—$(C_1\text{-}C_6)$ alkylaryl, aryl, heteroaryl, —$(CH_2)_n$-aryl, —$(CH_2)_n$-heteroaryl, —O-aryl, —O-heteroaryl, —S-aryl, —S-heteroaryl, each alkyl, aryl, cycloalkyl, heterocycloalkyl, heteroaryl, alkenyl, or alkynyl optionally substituted with one or more of $R_{13}$;

$R_{13}$ is halogen, —O—$(C_1\text{-}C_6)$ alkyl, —$CO_2H$, —OH, —$CF_3$, hydrogen, $(C_1\text{-}C_6)$ alkyl, aryl, heteroaryl, $(C_2\text{-}C_6)$ alkenyl, $(C_2\text{-}C_6)$ alkynyl, cycloalkyl, cycloalkyl substituted with —OH, aryl substituted with —$NH_2$, aryl substituted with —O—$(C_1\text{-}C_6)$ alkyl, —$(CH_2)_n$-aryl, or —$(CH_2)_n$-heteroaryl;

$R_{14}$ and $R_{15}$ are each independently hydrogen, $(C_1\text{-}C_6)$ alkyl, aryl, heteroaryl, $(C_2\text{-}C_6)$ alkenyl, $(C_2\text{-}C_6)$ alkynyl, cycloalkyl, heterocycloalkyl, —$(CH_2)_n$-aryl, bicyclic aryl, tricyclic aryl, bicyclic heteroaryl, or tricyclic heteroaryl; each alkyl, aryl, cycloalkyl, heterocycloalkyl, or heteroaryl optionally substituted with one or more $R_{12}$; or $R_{14}$ and $R_{15}$ together may form a five- to seven-membered cyclic group containing up to 3 heteroatoms selected from N, O, or S;

$R_{16}$ is $(C_1\text{-}C_6)$ alkyl;

$PG_1$ is an amine protecting group;

$PG_2$ is a carboxylic acid protecting group; and n is 0, 1, 2, 3, or 4.

The compounds of formula (I) through (VI) include enantiomerically pure compounds and/or sensitive protecting groups. Advantageously, the present invention provides methods for preparing such compounds substantially free of their corresponding opposite enantiomers and without disturbing the protecting groups when such groups are needed.

In one embodiment, the present invention is directed to a method of preparing a compound of formula (I):

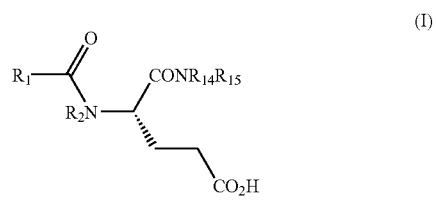

(I)

comprising:

a) treating a compound of formula (II),

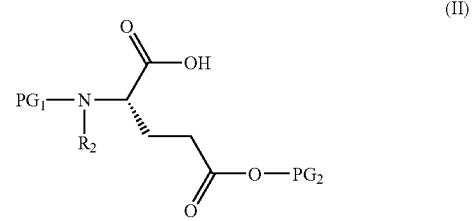

(II)

with an alkyl chloroformate of formula (III) and a base,

(III)

to provide a compound of the formula (IV);

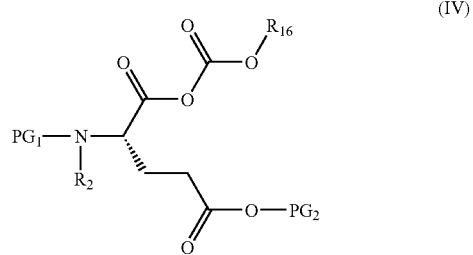

(IV)

b) treating the compound of formula (IV) with an amine having the formula of $HNR_{14}R_{15}$ or a pharmaceutically acceptable salt thereof;

to give a compound of formula (V);

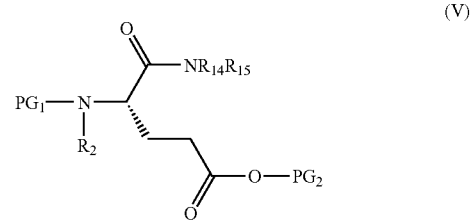

(V)

c) deprotecting the amine protecting group of the compound of formula (V) to give a compound of formula (VI); and

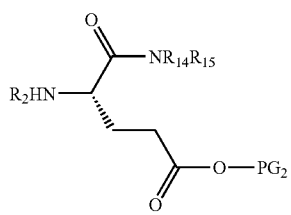

(VI)

d) treating the compound of formula (VI) with an acid chloride having the formula $R_1C(=O)Cl$ in the presence of a base to give a compound of formula (VII); and

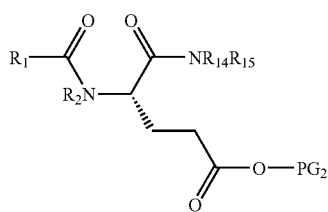

(VII)

e) deprotecting the carboxylic acid protecting group of the compound of formula (VII) via hydrolysis to give the to compound of formula (I).

In another embodiment, the present invention is directed to a method for preparing a compound of the formula (IV),

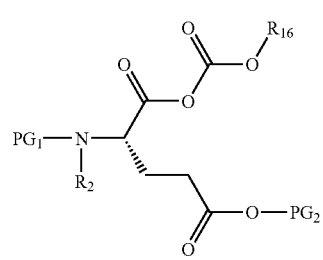

(IV)

comprising treating a compound of formula (II),

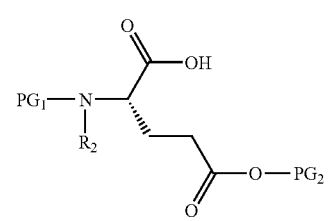

(II)

with an alkyl chloroformate of formula (III) and a base,

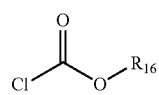

(III)

to provide the compound of formula (IV).

In yet another embodiment, the present invention is directed to a method for preparing a compound of formula (V),

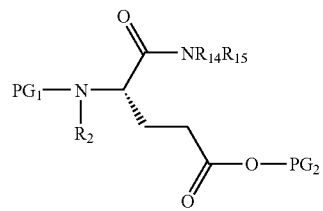

(V)

comprising:

a) treating a compound of formula (II),

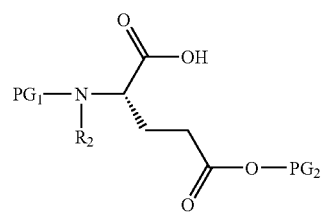

(II)

with an alkyl chloroformate of formula (III) and a base,

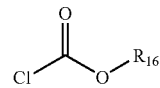

(III)

to provide a compound of the formula (IV); and

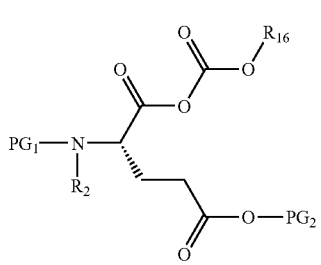

(IV)

b) treating the compound of formula (IV) with an amine having the formula of $HNR_{14}R_{15}$ or a pharmaceutically acceptable salt thereof;

to give a compound of formula (V).

In yet another embodiment, the present invention is directed to a method for preparing a compound of formula (VI), comprising:
a) treating a compound of formula (II),

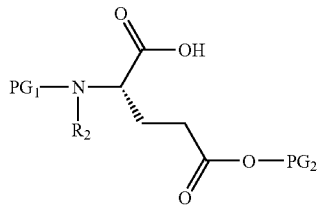
(II)

with an alkyl chloroformate of formula (III) and a base,

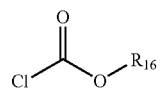
(III)

to provide a compound of the formula (IV);

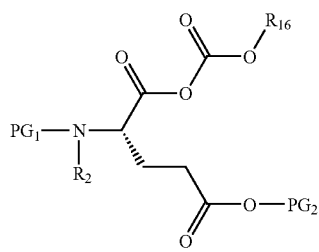
(IV)

b) treating the compound of formula (IV) with an amine having the formula of $HNR_{14}R_{15}$ or a pharmaceutically acceptable salt thereof;
to give a compound of formula (V); and

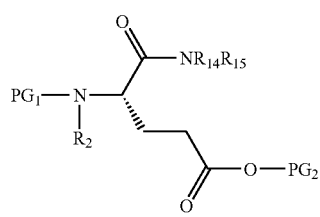
(V)

c) deprotecting the amine protecting group of the compound of formula (V) to give a compound of formula (VI).

In yet another embodiment, the present invention is directed to a method for preparing a compound of formula (VII), comprising:
a) treating a compound of formula (II),

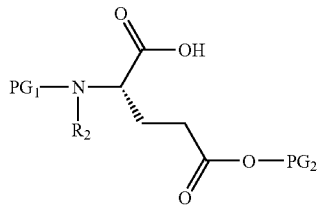
(II)

with an alkyl chloroformate of formula (III) and a base,

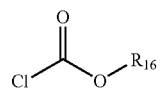
(III)

to provide a compound of the formula (IV);

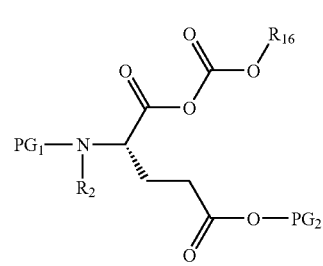
(IV)

b) treating the compound of formula (IV) with an amine having the formula of $HNR_{14}R_{15}$ or a pharmaceutically acceptable salt thereof;
to give a compound of formula (V);

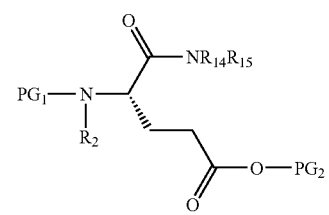
(V)

c) deprotecting the amine protecting group of the compound of formula (V) to give a compound of formula (VI); and

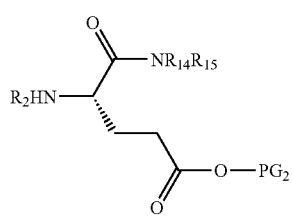
(VI)

d) treating the compound of formula (VI) with an acid chloride having the formula $R_1C(=O)Cl$ in the presence of a base to give a compound of formula (VII).

In one further embodiment, the present invention is directed to a compound of formula (IV),

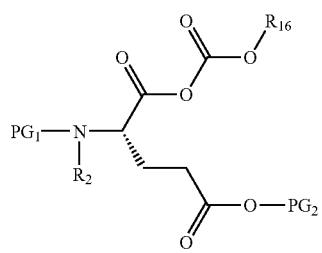

wherein $R_2$ is hydrogen, $(C_1-C_6)$ alkyl, $(C_2-C_6)$ alkenyl, $(C_2-C_6)$ alkynyl, $-(CH_2)_nR_{11}$, $-OH$, or $-O-(C_1-C_6)$ alkyl;

$R_{11}$ is aryl, heteroaryl, or cycloalkyl;

n is 0, 1, 2, 3, or 4;

$R_{16}$ is $(C_1-C_6)$ alkyl;

$PG_1$ is an amine protecting group; and $PG_2$ is a carboxylic acid protecting group.

In another embodiment, the present invention is directed to a compound of formula (IV), wherein $R_2$ is hydrogen; and $R_{16}$ is methyl, ethyl, propyl, isopropyl, butyl, or isobutyl.

In yet another embodiment, the present invention is directed to a compound of formula (IV), wherein $R_2$ is hydrogen; $R_{16}$ is methyl, ethyl, propyl, isopropyl, butyl, or isobutyl; $PG_1$ is Fmoc; and $PG_2$ is t-butyl.

In one further embodiment, the present invention is directed to a compound of formula (I),

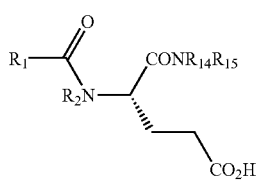

prepared by the method comprising:

a) treating a compound of formula (II),

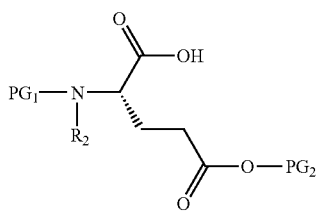

with an alkyl chloroformate of formula (III) and a base,

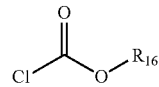

to provide a compound of the formula (IV);

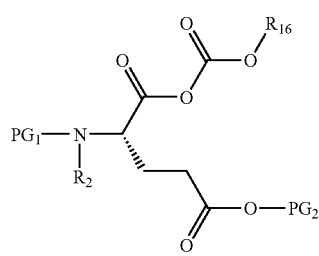

b) treating the compound of formula (IV) with an amine having the formula of $HNR_{14}R_{15}$ or a pharmaceutically acceptable salt thereof;

to give a compound of formula (V);

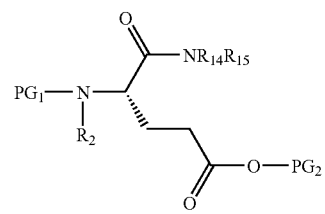

c) deprotecting the amine protecting group of the compound of formula (V) to give a compound of formula (VI); and

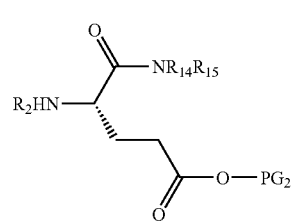

d) treating the compound of formula (VI) with an acid chloride having the formula $R_1C(=O)Cl$ in the presence of a base to give a compound of formula (VII); and

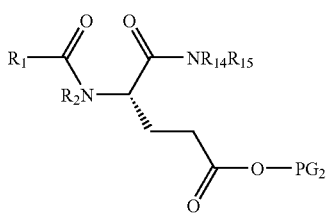

e) deprotecting the carboxylic acid protecting group of the compound of formula (VIII) via hydrolysis to give the to compound of formula (I).

In one further embodiment, the present invention is directed to a compound of formula (Ia):

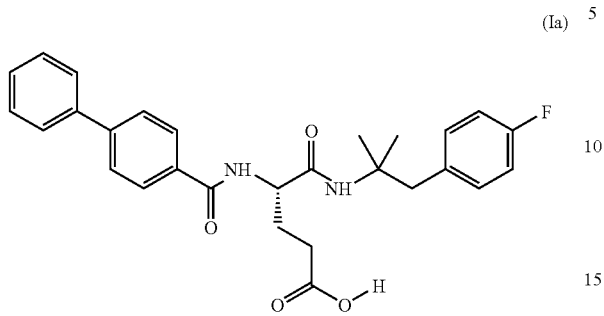
(Ia)

prepared by the method comprising:

a) treating a compound of formula (IIa),

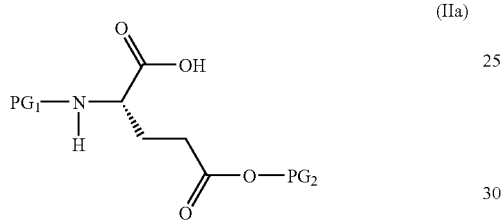
(IIa)

with an alkyl chloroformate of formula (III) and a base,

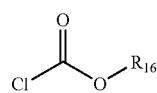
(III)

to provide a compound of the formula (IVa);

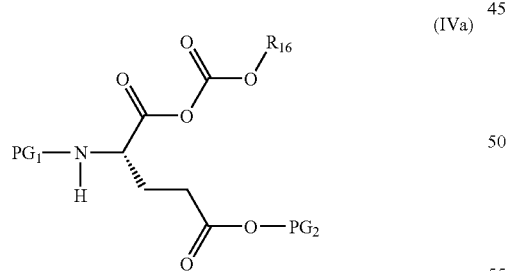
(IVa)

b) treating the compound of formula (IVa) with an amine having the formula of

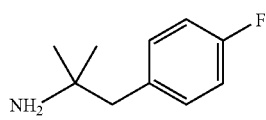

or a pharmaceutically acceptable salt thereof; to give a compound of formula (Va);

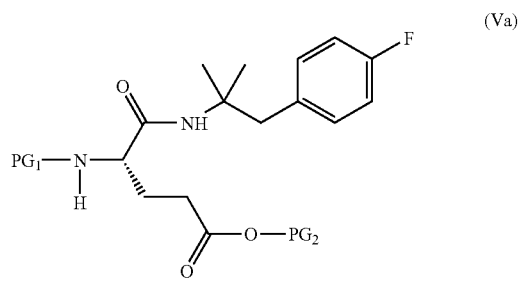
(Va)

c) deprotecting the amine protecting group of the compound of formula (Va) to give a compound of formula (VIa); and

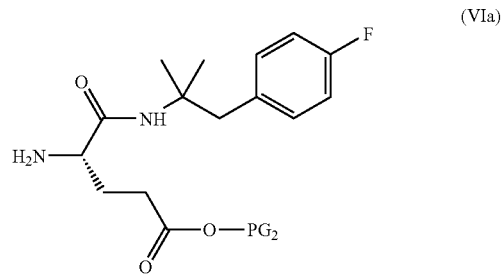
(VIa)

d) treating the compound of formula (VIa) with an acid chloride having the formula of

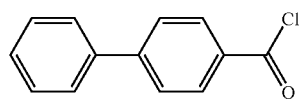

in the presence of a base to give a compound of formula (VIIa); and

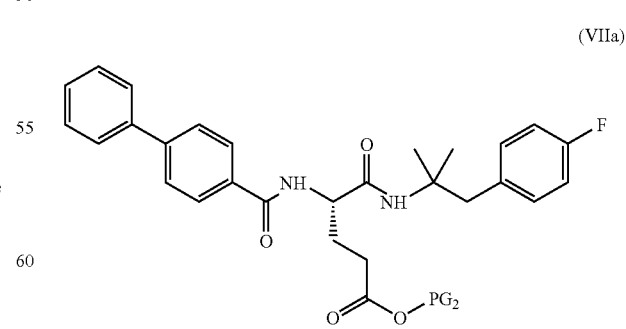
(VIIa)

e) deprotecting the carboxylic acid protecting group of the compound of formula (VIIa) via hydrolysis to give the to compound of formula (Ia).

In another embodiment, the present invention is directed to a method for preparing a compound of formula (Ia),

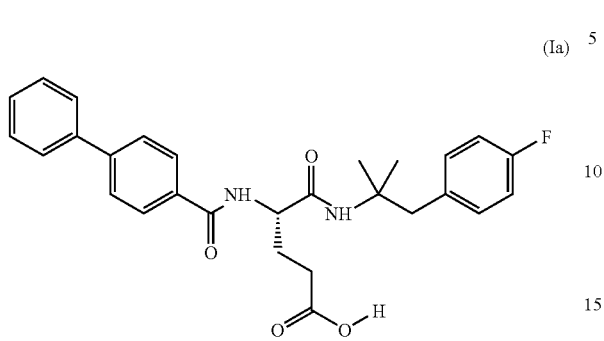
(Ia)

comprising:

a) treating a compound of formula (IIa),

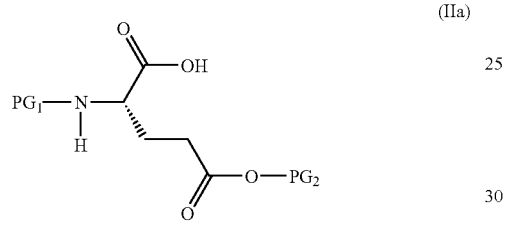
(IIa)

with an alkyl chloroformate of formula (III) and a base,

(III)

to provide a compound of the formula (IVa);

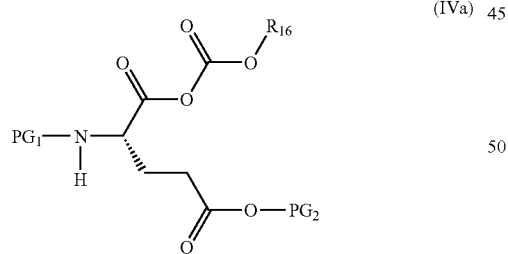
(IVa)

b) treating the compound of formula (IVa) with an amine having the formula of

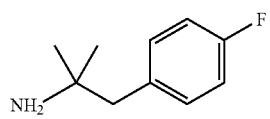

or a pharmaceutically acceptable salt thereof;

to give a compound of formula (Va);

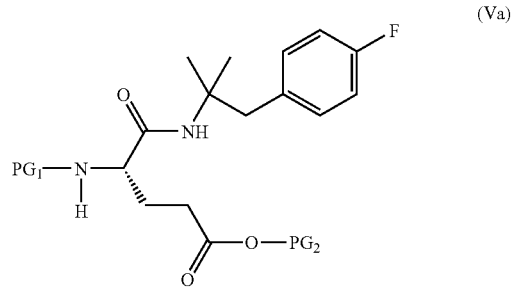
(Va)

c) deprotecting the amine protecting group of the compound of formula (Va) to give a compound of formula (VIa); and

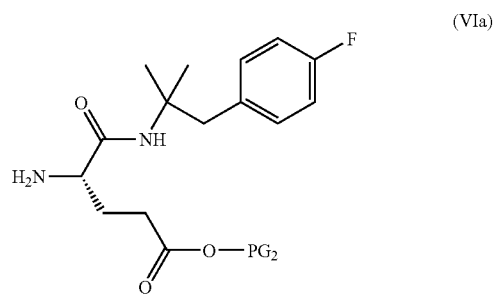
(VIa)

d) treating the compound of formula (VIa) with an acid chloride having the formula of

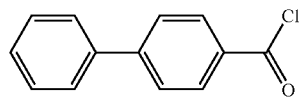

in the presence of a base to give a compound of formula (VIa); and

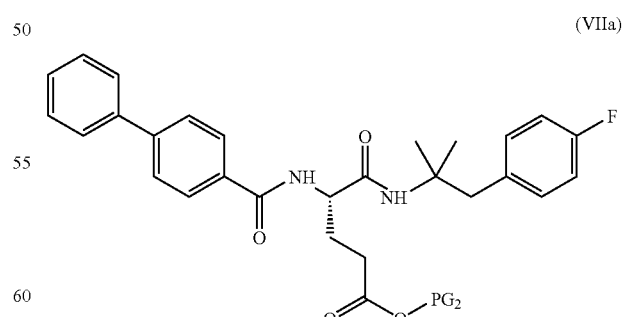
(VIIa)

e) deprotecting the carboxylic acid protecting group of the compound of formula (VIIa) via hydrolysis to give the to compound of formula (Ia).

In one further embodiment, the present invention is directed to a method for preparing a compound of formula (I),

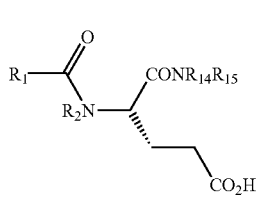
(I)

comprising:

a) treating a compound of formula (II),

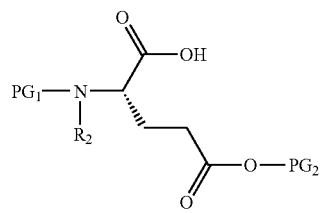
(II)

with a chlorinating reagent such as oxalyl chloride or thionyl chloride, optionally in the presence of a catalytic amount of DMF, to provide a compound of the formula (IVb);

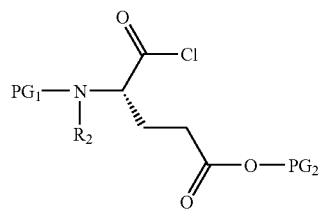
(IVb)

b) treating the compound of formula (IVb) with an amine having the formula of $HNR_{14}R_{15}$ or a pharmaceutically acceptable salt thereof;

to give a compound of formula (V);

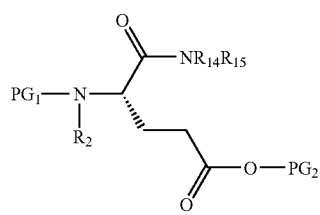
(V)

c) deprotecting the amine protecting group of the compound of formula (V) to give a compound of formula (VI);

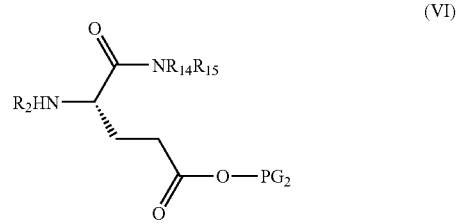
(VI)

d) treating the compound of formula (VI) with an acid chloride having the formula $R_1C(=O)Cl$ in the presence of a base to give a compound of formula (VII); and

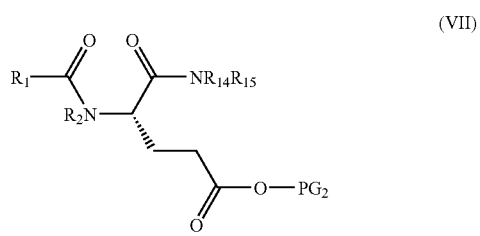
(VII)

e) deprotecting the carboxylic acid protecting group of the compound of formula (VII) via hydrolysis to give the to compound of formula (I).

In another embodiment, the present invention is directed to a compound of formula (I),

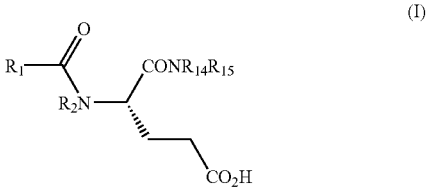
(I)

prepared by the method comprising:

a) treating a compound of formula (II),

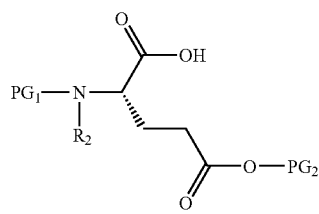
(II)

with a chlorinating reagent such as oxalyl chloride or thionyl chloride, optionally in the presence of a catalytic amount of DMF, to provide a compound of the formula (UVb);

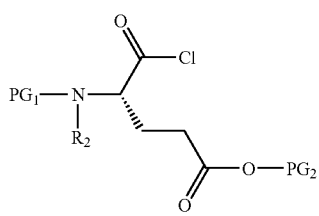

b) treating the compound of formula (UVb) with an amine having the formula of $HNR_{14}R_{15}$ or a pharmaceutically acceptable salt thereof;
to give a compound of formula (V);

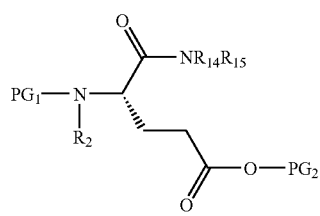

c) deprotecting the amine protecting group of the compound of formula (V) to give a compound of formula (VI); and

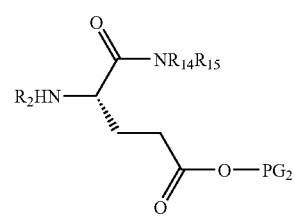

d) treating the compound of formula (VI) with an acid chloride having the formula $R_1C(\!=\!O)Cl$ in the presence of a base to give a compound of formula (VII); and

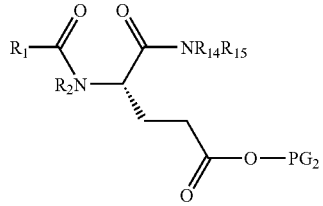

e) deprotecting the carboxylic acid protecting group of the compound of formula (VII) via hydrolysis to give the to compound of formula (I).

Methods of Preparation

The compounds and pharmaceutically acceptable salts of compounds of the present invention can be prepared using a variety of methods starting from commercially available compounds, known compounds, or compounds prepared by known methods. General synthetic routes to many of the compounds of the invention are included in the following schemes. It is understood by those skilled in the art that protection and deprotection steps not shown in the Schemes may be required for these syntheses, and that the order of steps may be changed to accommodate functionality in the target molecule.

Scheme I demonstrates the synthesis of the compound of formula (I) from the compound of formula (II). The compound of formula (II) can react with a $(C_1\text{-}C_6)$ alkyl chloroformate of formula (III) such as methyl chloroformate, ethyl chloroformate, propyl chloroformate, isopropyl chloroformate, butyl chloroformate, isobutyl chloroformate, followed by treatment with a base such as triethylamine, diisopropylethylamine, pyridine, N-methylmorpholine, sodium bicarbonate, or potassium carbonate, to provide a compound of formula (IV). The compound of formula (IV) can further react with an amine of formula $HNR_{14}R_{15}$ to afford a compound of formula (V). Treatment of the compound of formula (V) with an amine base can cleave the amine protecting group of $PG_1$ to provide a compound of formula (VI). A variety of amine bases may be used, including for example, diethylamine, piperidine, morpholine, dicyclohexylamine, p-dimethylaminopyridine, or diisopropylethylamine in a solvent, such as acetonitrile or DMF.

Coupling of the compound of formula (VI) with an acid of formula $R_1COCl$ in the presence of a base affords a compound of formula (VII). The carboxylic acid protecting group of the compound of formula (VII) can be cleaved via hydrolysis to give the compound of formula (I). The hydrolysis step can be carried out using TFA, NaOH, LiOH, potassium carbonate, or the like.

Scheme 1

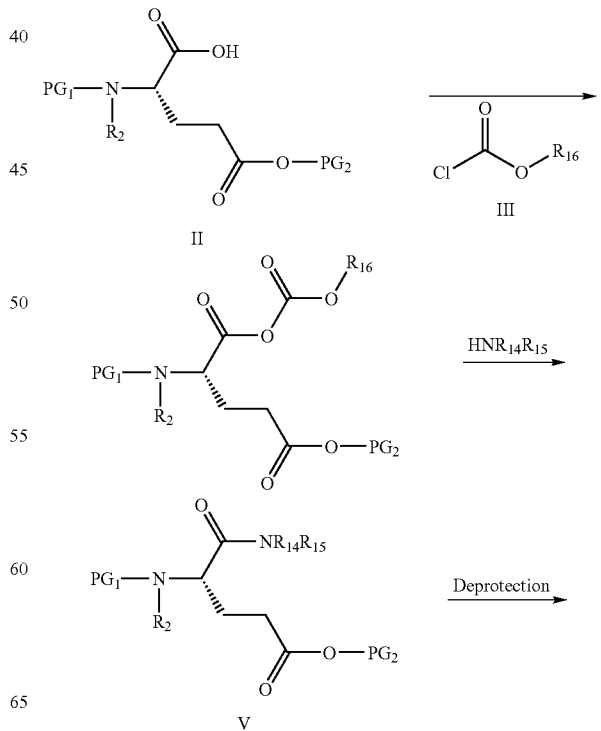

-continued

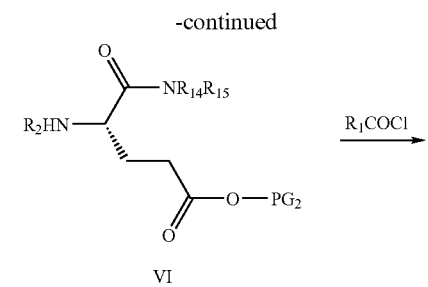
VI

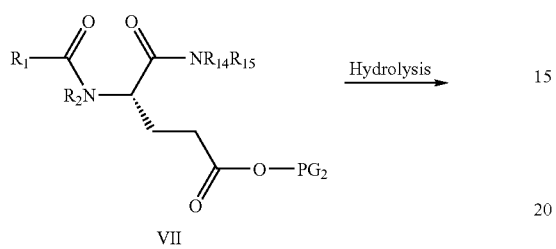
VII

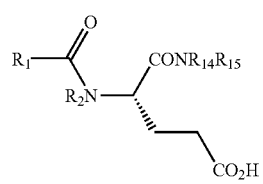
I

Scheme 1a describes an alternative synthesis of the compound of formula (V). Treatment of the compound of formula (II) with a chlorinating reagent, such as oxalyl chloride, thionyl chloride, etc., and optionally in the presence of a catalytic amount of DMF, provides an acid chloride of formula (IVb), which can be coupled with an amine of formula $HNR_{14}R_{15}$, to give the compound of formula (V).

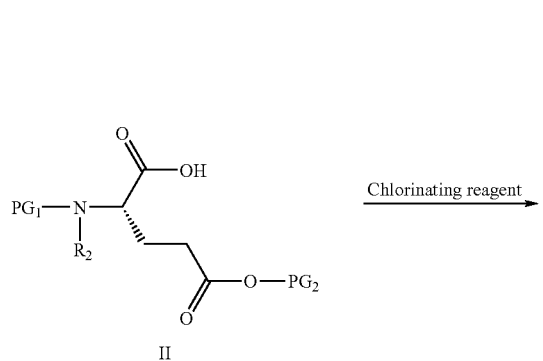

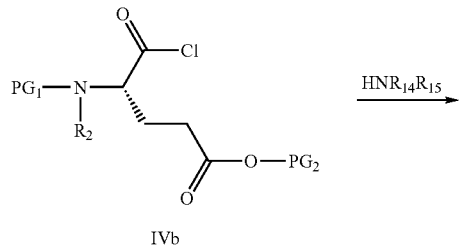
IVb

-continued

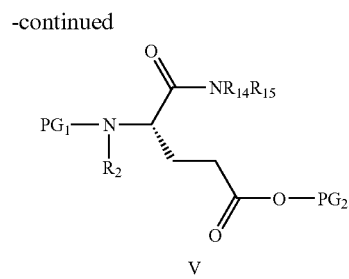
V

Scheme 2 further demonstrates the synthesis of a compound of formula (Ia) from a compound of formula (IIa), using an analogous method as that is described in Scheme 1. Alternatively, the compound of formula (Va) can be prepared from the compound of formula (IIa) in accordance with Scheme 2a, which uses a similar method as that of Scheme 1a.

Scheme 2

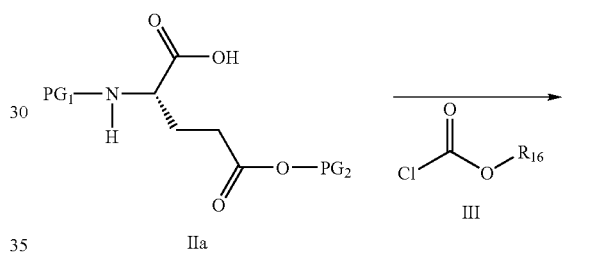
IIa          III

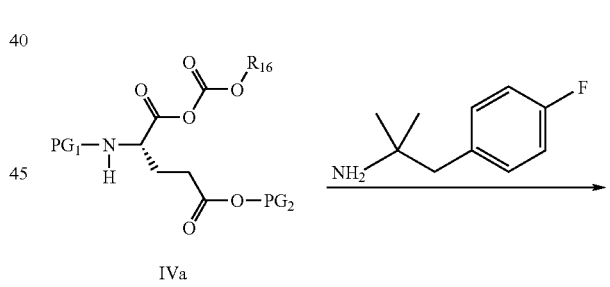
IVa

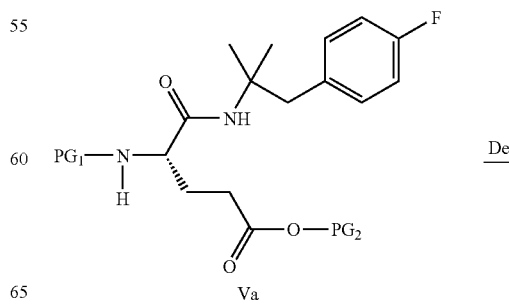
Va

-continued
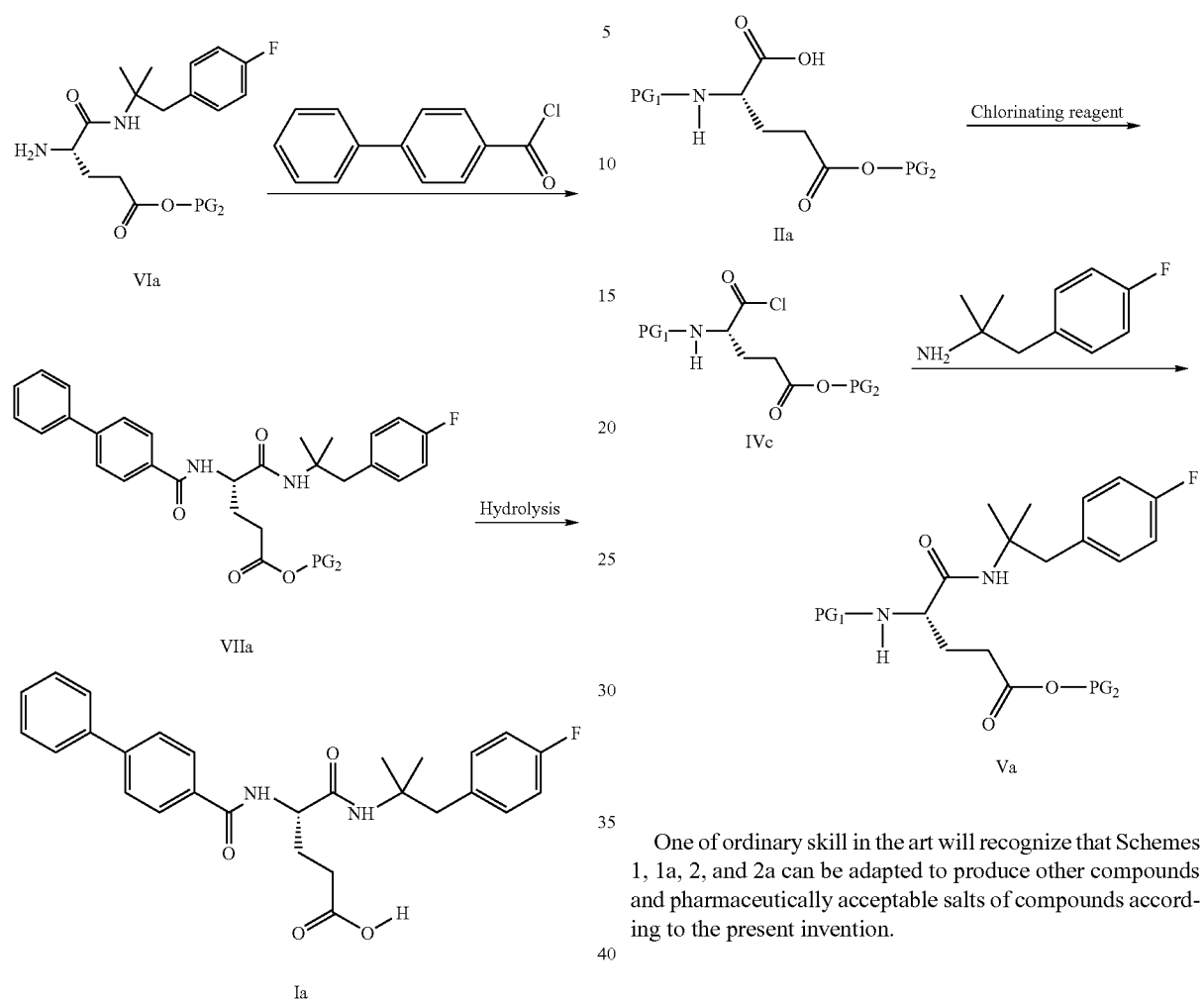
One of ordinary skill in the art will recognize that Schemes 1, 1a, 2, and 2a can be adapted to produce other compounds and pharmaceutically acceptable salts of compounds according to the present invention.
EXAMPLES
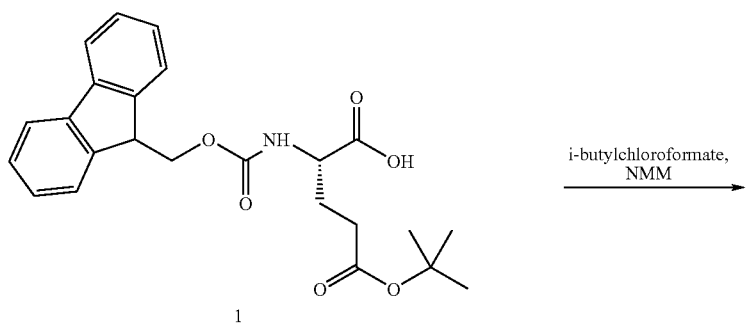

-continued

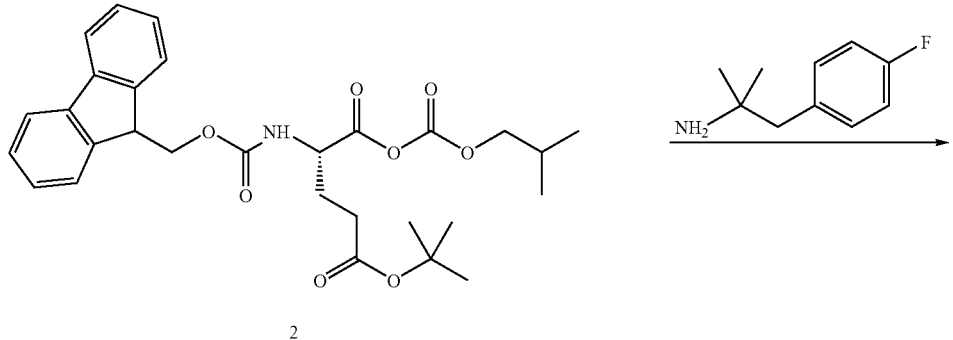

2

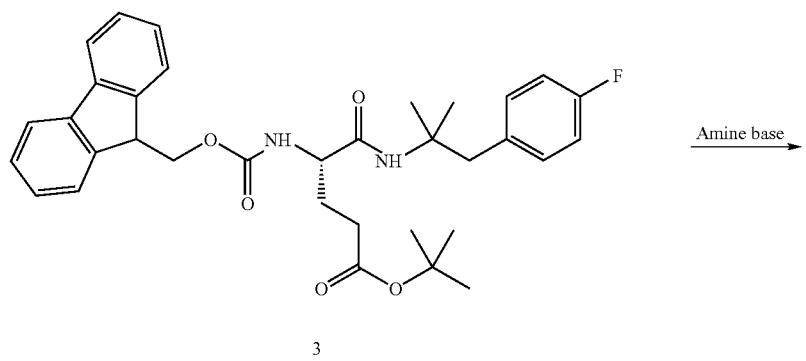

3

Amine base

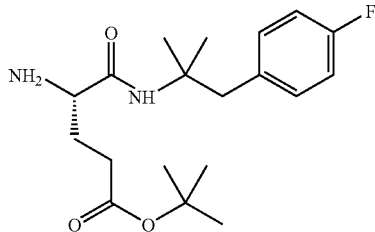

4

Example 1

Preparation of 4(S)-Amino-4-[2-(4-fluoro-phenyl)-1,1-dimethyl-ethylcarbamoyl]-butyric acid tert-butyl ester (Compound 4)

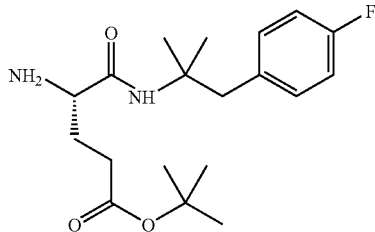

Compound 1 [2(S)-(9H-Fluoren-9-ylmethoxycarbonylamino)-pentanedioic acid 5-tert-butyl ester] (161 g) was suspended in toluene (1 L). Iso-Butyl chloroformate (59.5 g), N-methylmorpholine (91.7 g) and 2-(4-Fluoro-phenyl)-1,1-dimethyl-ethylamine (88.7 g as hydrochloride salt) were added sequentially at 5 to 15° C. After the reaction was completed in about 1 h, toluene solution was washed with water, treated with diethylamine (66.2 g) and stirred at ambient temperature until deprotection was complete (2 to 12 h). The product was extracted with 2N hydrochloric acid and by-products were removed by extraction with heptane. The resulting aqueous solution was treated with potassium carbonate and extracted with t-butyl methyl ether (TBME) to afford Compound 4 as a solution in TBME.

Alternative Synthesis of Compound 4: Compound 1 [2(S)-(9H-Fluoren-9-ylmethoxycarbonylamino)-pentanedioic acid 5-tert-butyl ester] (1 g, 2.3 mmol) was combined with THF (5 mL) and 1 drop of DMF and cooled to 0 C. Oxalyl chloride (0.328 g, 2.5 mmol) was added and the solution was stirred for about 30 min. before it was concentrated to form foam. The resulting foam was dissolved in THF and 2-(4-Fluoro-phenyl)-1,1-dimethyl-ethylamine (0.864 g, 4.6 mmol) was added. After the reaction was completed as determined by HPLC, Compound 4 was isolated following regular aqueous work-up.

Example 2

Preparation of 4(S)-[(Biphenyl-4-carbonyl)-amino]-4-[2-(4-fluoro-phenyl)-1,1-dimethyl-ethylcarbamoyl]-butyric acid tert-butyl ester (Compound 5)

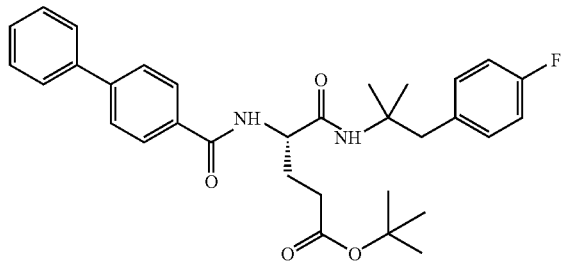

To the TBME solution of Compound 4 (561 g, strength 20%) were added triethylamine (64.6 g) and biphenyl carbonyl chloride (58.9 g, dissolved in THF) at 15 to 35° C. After the reaction was completed (1 to 18 h), the reaction mixture was washed with diluted HCl solution, sodium bicarbonate solution and water, concentrated, and Compound 5 was precipitated from the IPA/water mixture as white crystals (131 g, 77% yield). NMR data: 1.35-s, 6H, $CH_3$; 1.40-s, 9H, $CH_3$; 2.10-m, 2H, $CH_2$; 2.20-2.30-m, 2H, $CH_2$, 2.90-3.10-m, 2H, $CH_2$; 4.50-m, 1H, CH; 6.80-7.80-m, 13H, Ph; 7.90-d, 1H, NH.

Example 3

Preparation of 4(S)-[(Biphenyl-4-carbonyl)-amino]-4-[2-(4-fluoro-phenyl)-1,1-dimethyl-ethylcarbamoyl]-butyric acid (Compound 6)

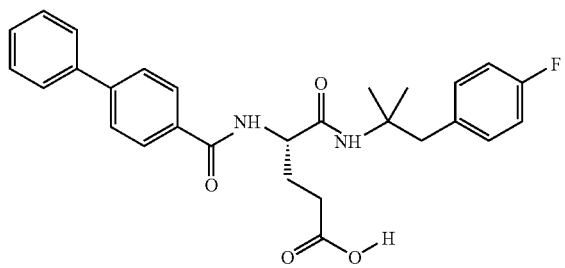

To a suspension of Compound 5 (100 g) in toluene (325 ml) were added trifluoroacetic acid (TFA, 313 g) at 5 to 20° C. The resulting solution was stirred at ambient temperature until the reaction was completed (4 to 6 h). TFA was removed by vacuum distillation, the solution diluted with ethyl acetate, washed with aqueous potassium acetate, and crystallization was affected by adding heptane to afford Compound 6 as white solid (82.7 g, yield 92%; Purity—99.8% (HPLC area %); Strength—98.0%; ee—99.0%). NMR data: 1.37, 1.45-s, 6H, $CH_3$; 2.10-m, 2H, $CH_2$; 2.35-2.60-m, 2H, $CH_2$; 2.80-3.10-d, 2H, $CH_2$; 4.80-q, 1H, CH; 6.80-7.80-m, 13H, Ph; 7.90-s, 2H, NH.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:

1. A method for preparing a compound of formula (Ia), (Ia)

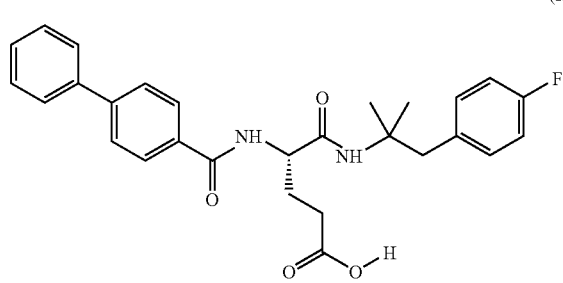

comprising:

a) treating a compound of formula (IIa), (IIa)

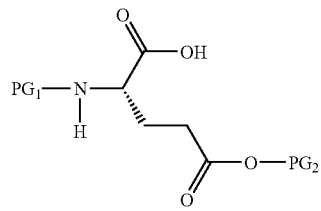

with an alkyl chloroformate of formula (III) and a base, (III)

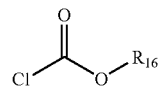

to provide a compound of the formula (IVa);

(IVa)

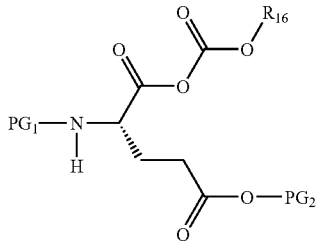

b) treating the compound of formula (IVa) with an amine having the formula of

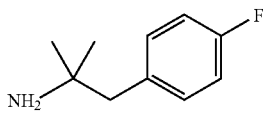

or a pharmaceutically acceptable salt thereof;
to give a compound of formula (Va);

(Va)

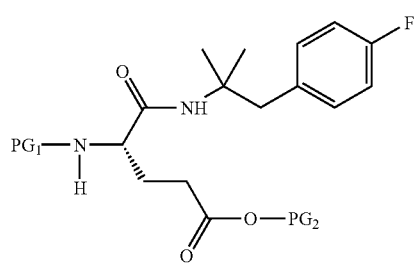

c) deprotecting the amine protecting group of the compound of formula (Va) to give a compound of formula (VIa); and (VIa)

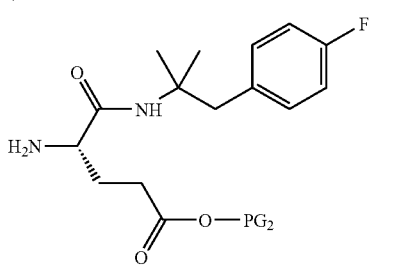

d) treating the compound of formula (VIa) with an acid chloride having the formula of

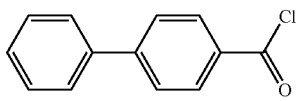

in the presence of a base to give a compound of formula (VIIa); and (VIIa)

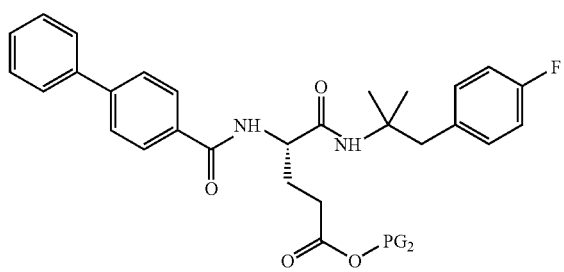

e) deprotecting the carboxylic acid protecting group of the compound of formula (VIIa) via hydrolysis to give the compound of formula (Ia), wherein:
PG$_1$ is an amine protecting group;
PG$_2$ is a carboxylic acid protecting group; and
R$_{16}$ is (C$_1$-C$_6$) alkyl.

2. A method for preparing a compound of formula (I), (I)

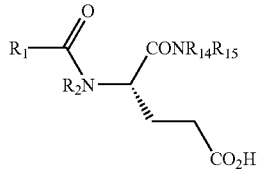

comprising
a) treating a compound of formula (II), (II)

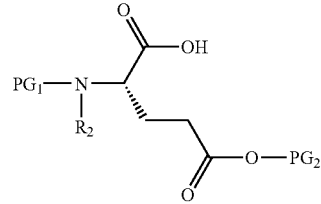

with oxalyl chloride of thionyl chloride, optionally in the presence of a catalytic amount of DMF, to provide a compound of the formula (IVb);

(IVb)

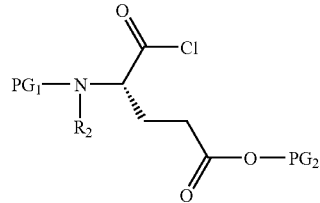

b) treating the compound of formula (IVb) with an amine having the formula of HNR$_{14}$R$_{15}$ or a pharmaceutically acceptable salt thereof; to give a compound of formula (V);

(V)

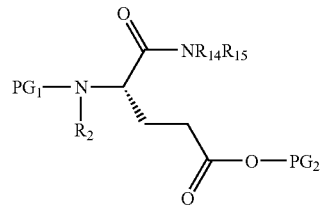

c) deprotecting the amine protecting group of the compound of formula (V) to give a compound of formula (VI);

(VI)

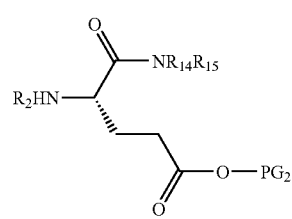

d) treating the compound of formula (VI) with an acid chloride having the formula $R_1C(=O)Cl$ in the presence of a base to give a compound of formula (VII); and

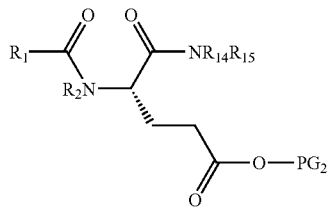

(VII)

e) deprotecting the carboxylic acid protecting group of the compound of formula (VII) via hydrolysis to give the compound of formula (I), wherein:

$R_1$ is biphenyl optionally substituted with one or more $R_6$, and when $R_1$ is substituted with more than one $R_6$, the substituents can be identical or different;

$R_2$ hydrogen;

$R_6$ is hydrogen or halogen;

$R_{12}$ is aryl or heteroaryl optionally substituted with one or more of $R_{13}$;

$R_{13}$ is halogen;

$R_{14}$ and $R_{15}$ are each independently hydrogen or $(C_1$-$C_6)$ alkyl optionally substituted with one or more $R_{12}$;

$PG_1$ is an amine protecting group; and $PG_2$ is a carboxylic acid protecting group.

* * * * *